(12) United States Patent
Lewkonya et al.

(10) Patent No.: US 12,156,997 B2
(45) Date of Patent: Dec. 3, 2024

(54) DUAL CHAMBER SYRINGE WITH A RESTRICTING ELEMENT AND METHODS OF USE THEREOF

(71) Applicant: Dali Medical Devices Ltd, Yavne (IL)

(72) Inventors: Gad Lewkonya, Neve Mivtach (IL); Ehoud Carmel, Yehud-Monosson (IL); Lior Raday, Kibbutz Bror-Hail (IL); David Daily, Herzliya (IL); Guy Keenan, Tel Aviv (IL); Nir Benarous, Holon (IL); Hagay Drori, Tel-Aviv (IL)

(73) Assignee: Dali Medical Devices Ltd, Yavne (IL)

( * ) Notice: Subject to any disclaimer, the term of this patent is extended or adjusted under 35 U.S.C. 154(b) by 230 days.

(21) Appl. No.: 17/492,612

(22) Filed: Oct. 3, 2021

(65) Prior Publication Data

US 2022/0111150 A1    Apr. 14, 2022

Related U.S. Application Data

(60) Provisional application No. 63/090,229, filed on Oct. 11, 2020.

(51) Int. Cl.
  *A61M 5/19* (2006.01)
  *A61M 5/31* (2006.01)
  *A61M 5/315* (2006.01)

(52) U.S. Cl.
  CPC .......... *A61M 5/31596* (2013.01); *A61M 5/19* (2013.01); *A61M 5/3137* (2013.01); *A61M 5/31511* (2013.01)

(58) Field of Classification Search
  CPC .. A61M 5/31596; A61M 5/19; A61M 5/3137; A61M 5/31511; A61M 5/31501;
  (Continued)

(56) References Cited

U.S. PATENT DOCUMENTS

2012/0316509 A1    12/2012  Kayser
2014/0236121 A1*   8/2014   Bar-Shalom ...... A61M 5/31596
                                                    604/518
(Continued)

FOREIGN PATENT DOCUMENTS

EP    2 257 323 B1    5/2019
WO    01/62319 A2     8/2001
(Continued)

OTHER PUBLICATIONS

U.S. Appl. No. 16/994,596, to the Applicant, filed Aug. 16, 2020, entitled "Dual Chamber Syringe and Methods of Use Thereof", presently unpublished.

*Primary Examiner* — Nathan R Price
*Assistant Examiner* — Haden Matthew Ritchie
(74) *Attorney, Agent, or Firm* — Naomi S. Rosenman-Helfand

(57)    ABSTRACT

A syringe assembly, comprising a syringe barrel having a forward end and a rearward end and being arranged along a longitudinal axis; a restricting element, moveably supported onto a portion of the syringe assembly and positionable in one of an injection disabling position and an injection enabling position in different operative orientations of the syringe assembly; a plunger rod assembly displaceable within the syringe barrel and operatively coupled with the restricting element; the plunger rod assembly having a restricting feature adapted to cooperate with the restricting element, such that when the restricting element in the injection disabling position, the plunger rod assembly is permitted to be displaced axially forwardly only up to a certain longitudinal extent relative to the syringe barrel and when the restricting element is in the injection enabling position, the plunger rod assembly is permitted to be further displaced axially forwardly relative to the syringe barrel.

17 Claims, 35 Drawing Sheets

(58) Field of Classification Search
CPC ........... A61M 2005/31508; A61M 2005/3151; A61M 2005/31598
See application file for complete search history.

(56) References Cited

U.S. PATENT DOCUMENTS

| | | | | |
|---|---|---|---|---|
| 2014/0316334 | A1* | 10/2014 | Holmqvist | A61M 5/284 |
| | | | | 604/220 |
| 2018/0169343 | A1* | 6/2018 | Rolfe | A61M 5/3148 |
| 2018/0264194 | A1* | 9/2018 | Larsen | A61M 5/2448 |
| 2022/0339360 | A1* | 10/2022 | Young | A61M 5/31505 |

FOREIGN PATENT DOCUMENTS

| | | |
|---|---|---|
| WO | 2006/066336 A1 | 6/2006 |
| WO | 2017077537 | 5/2017 |

* cited by examiner

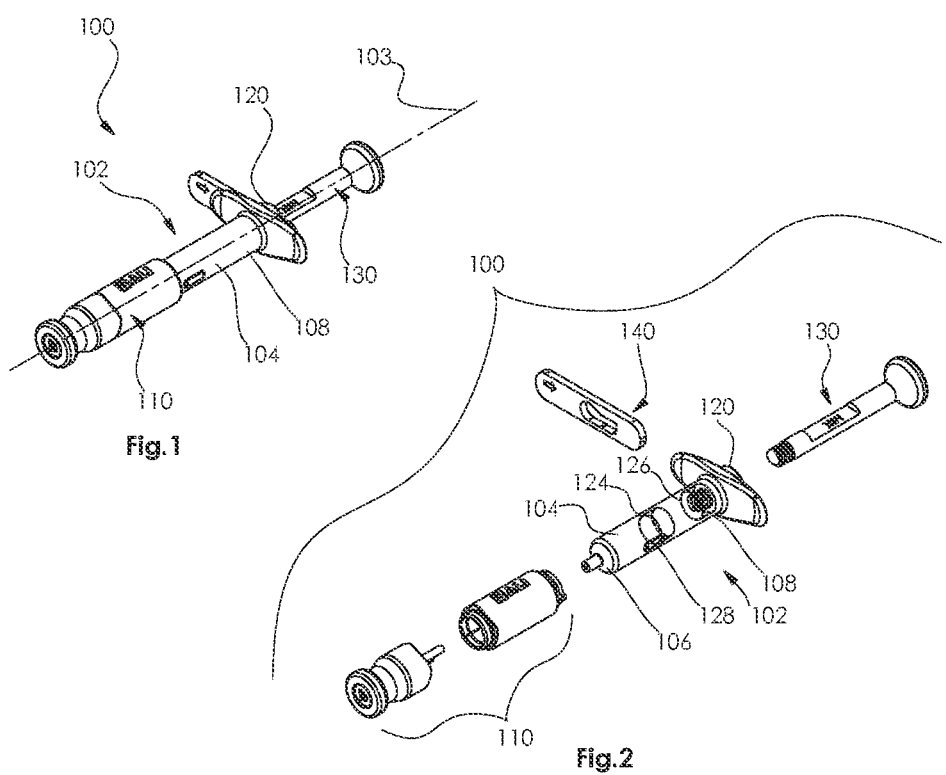

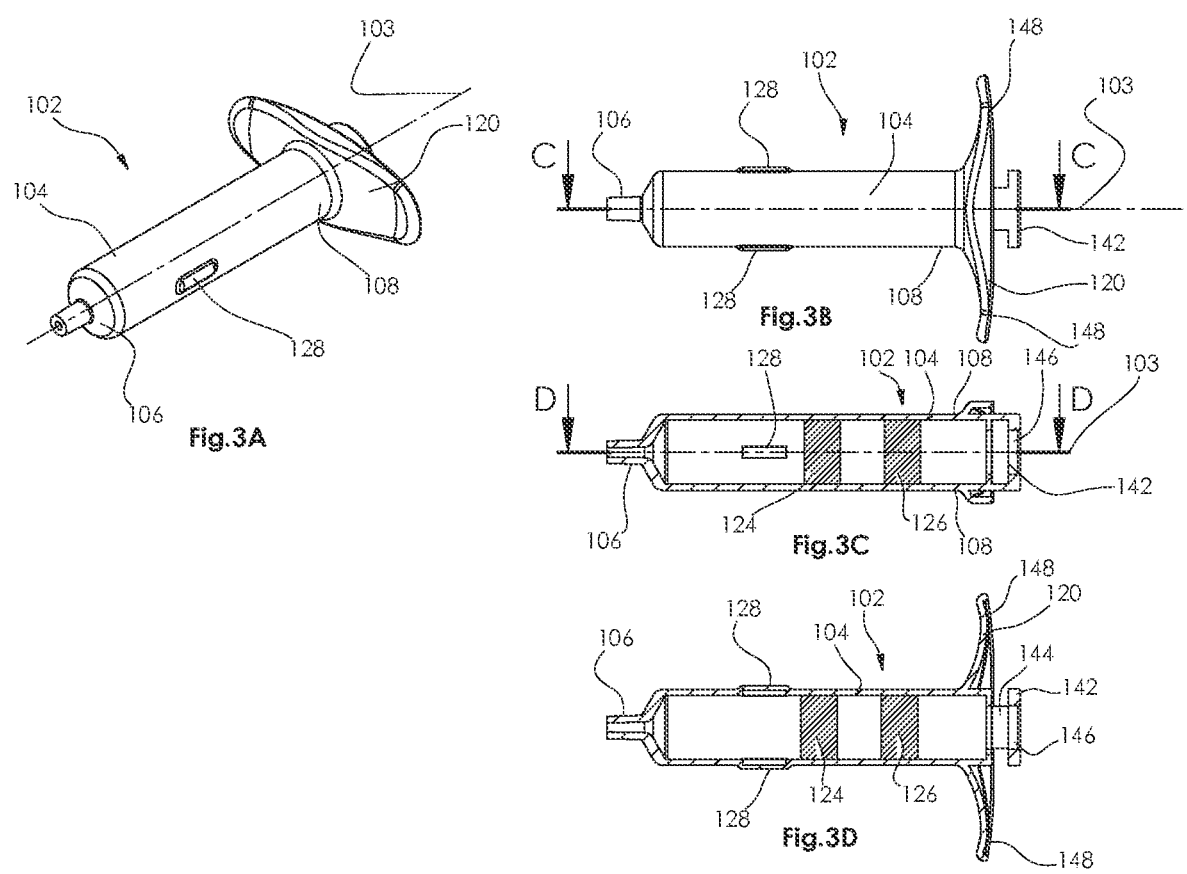

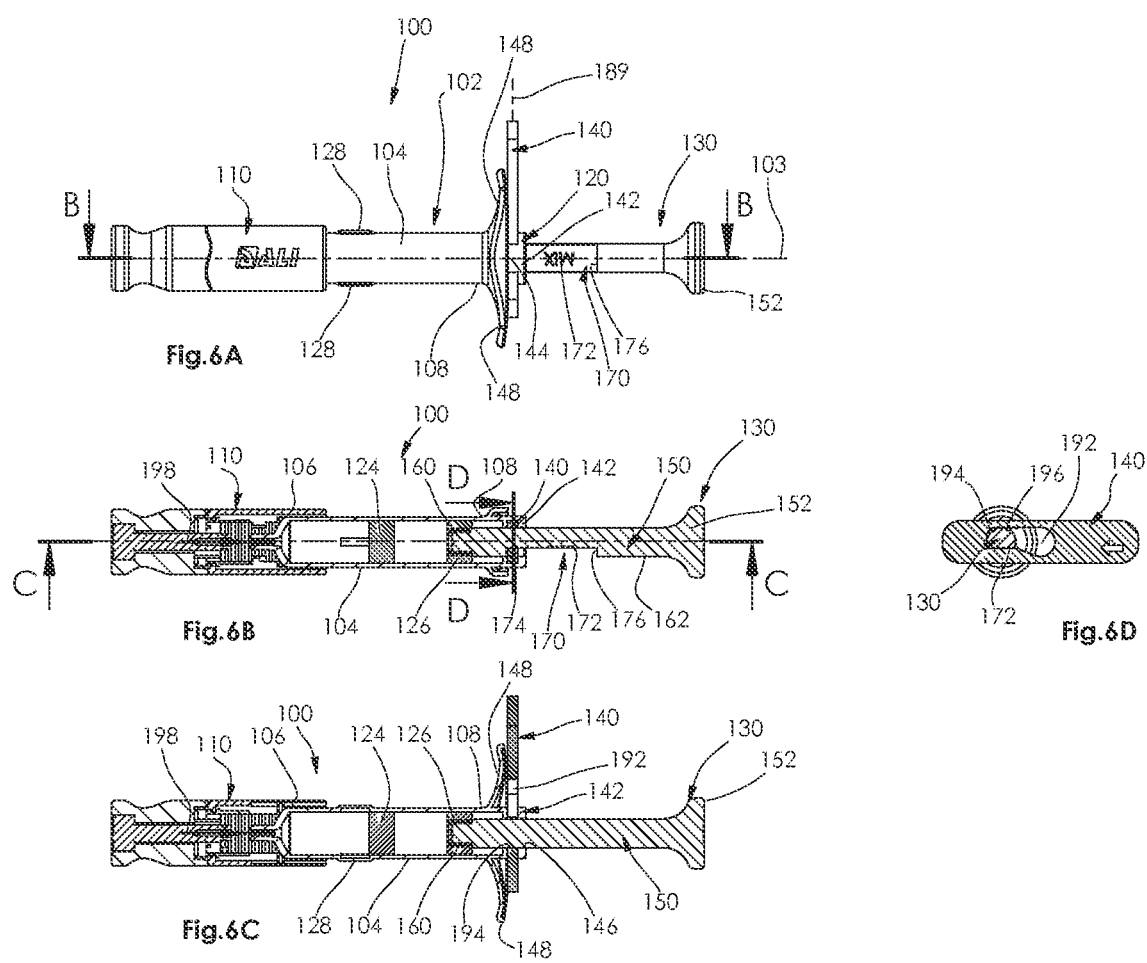

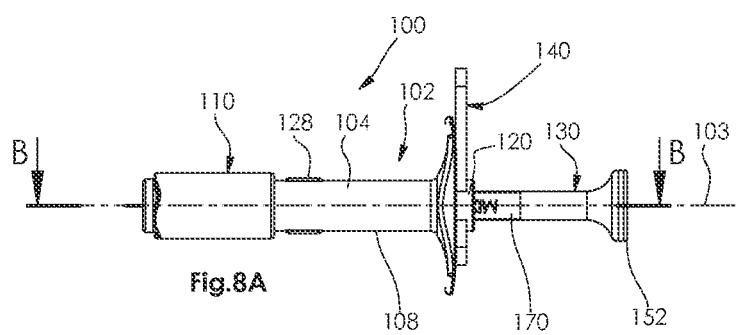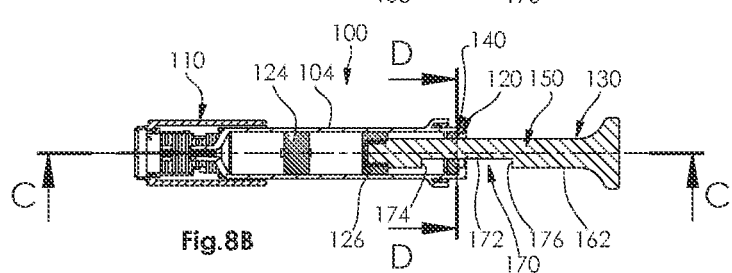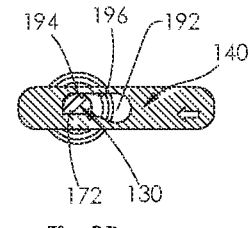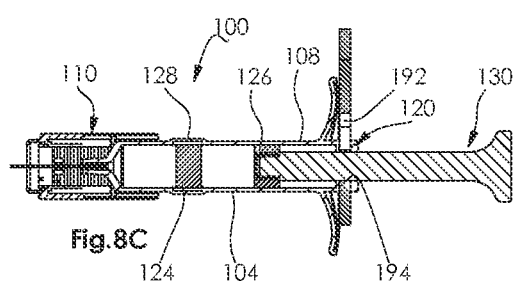

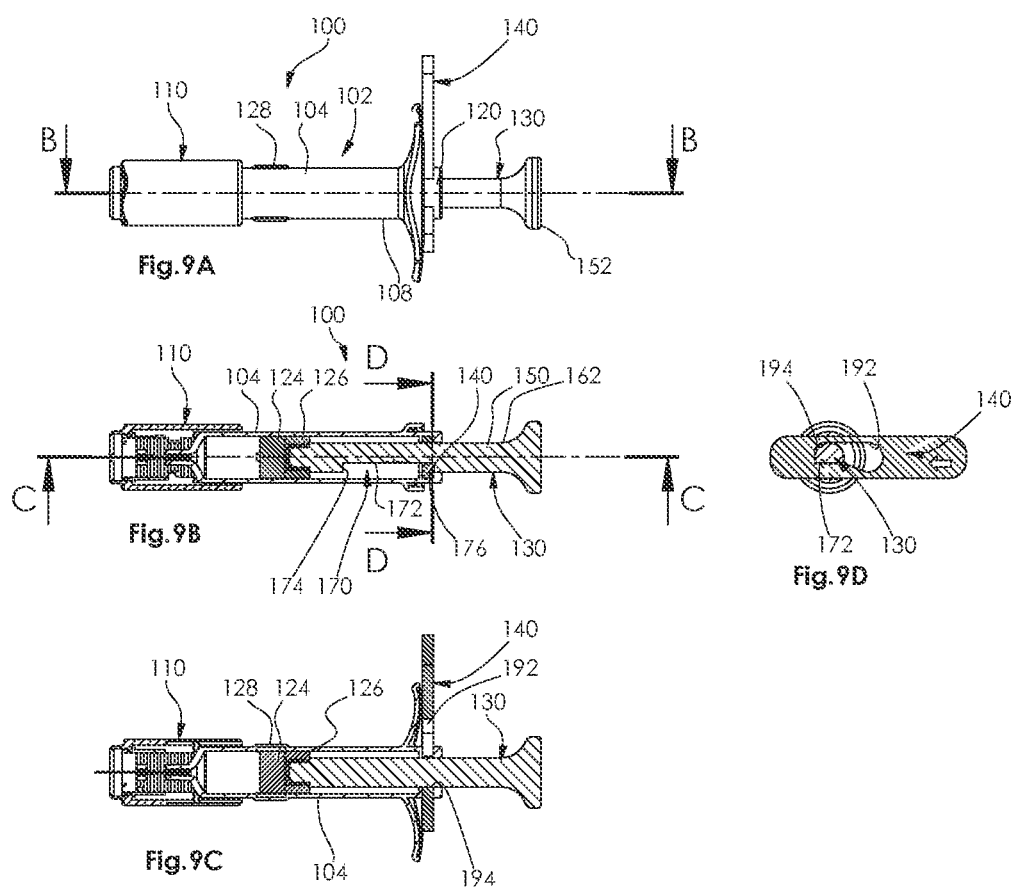

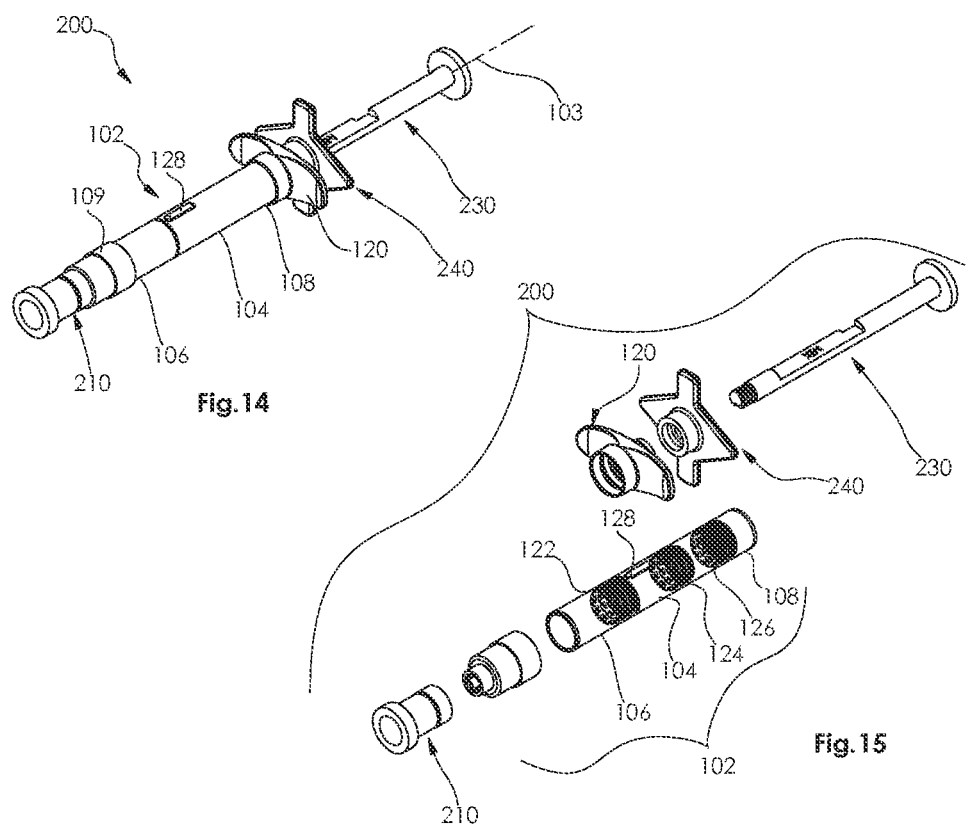

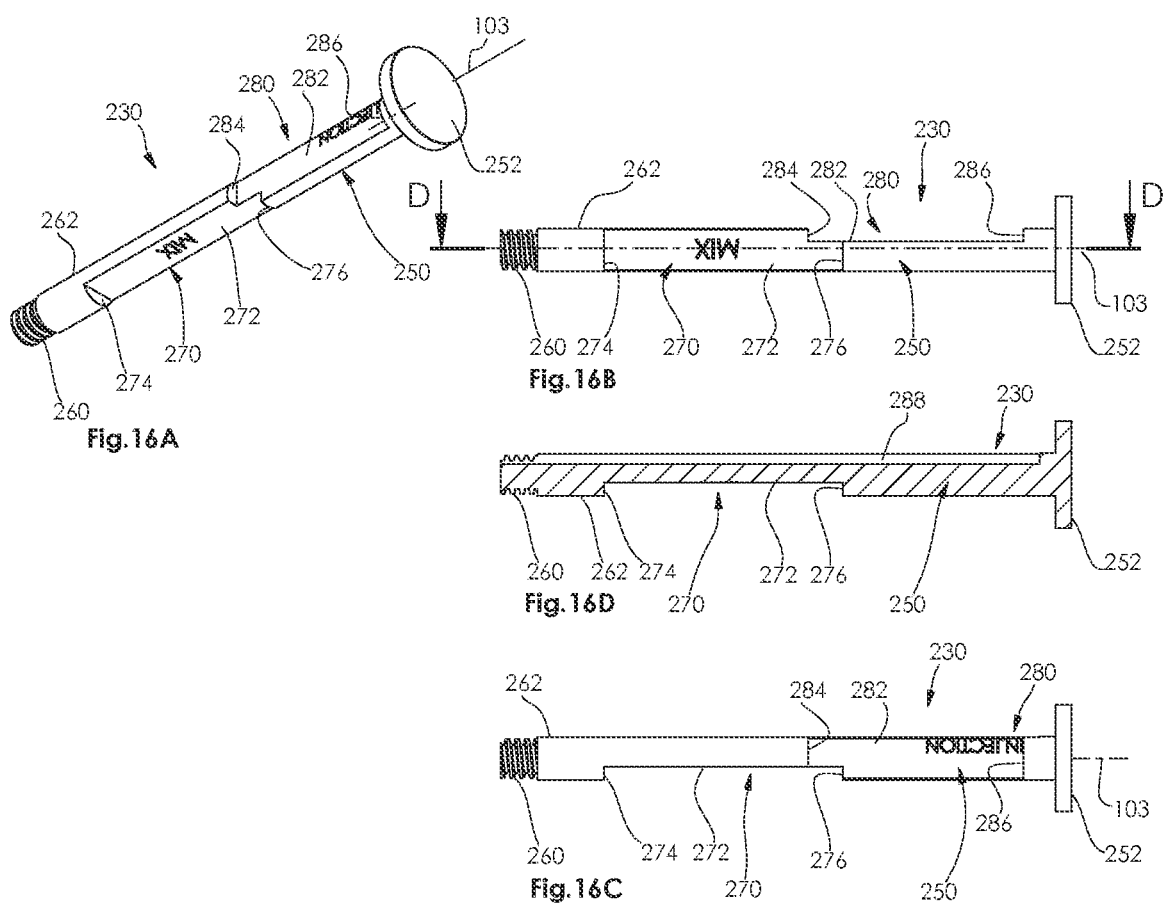

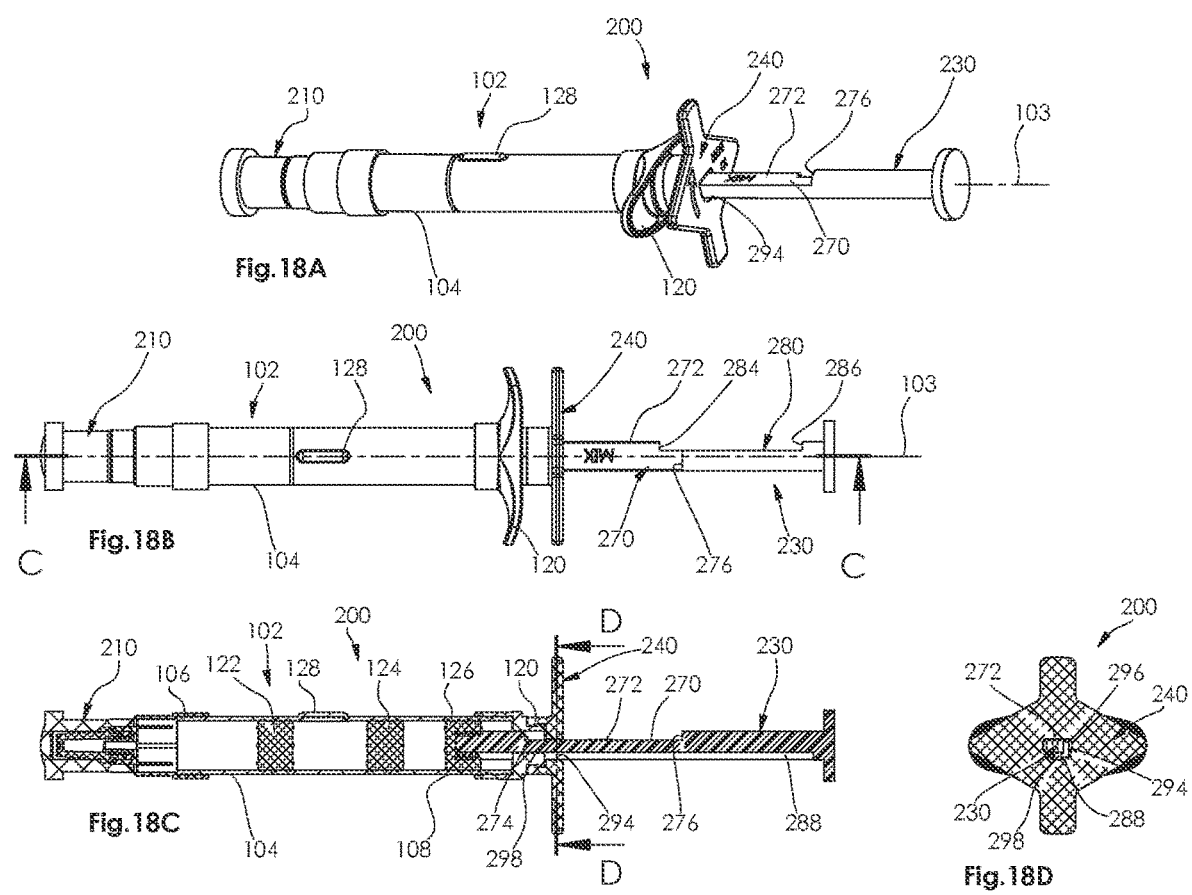

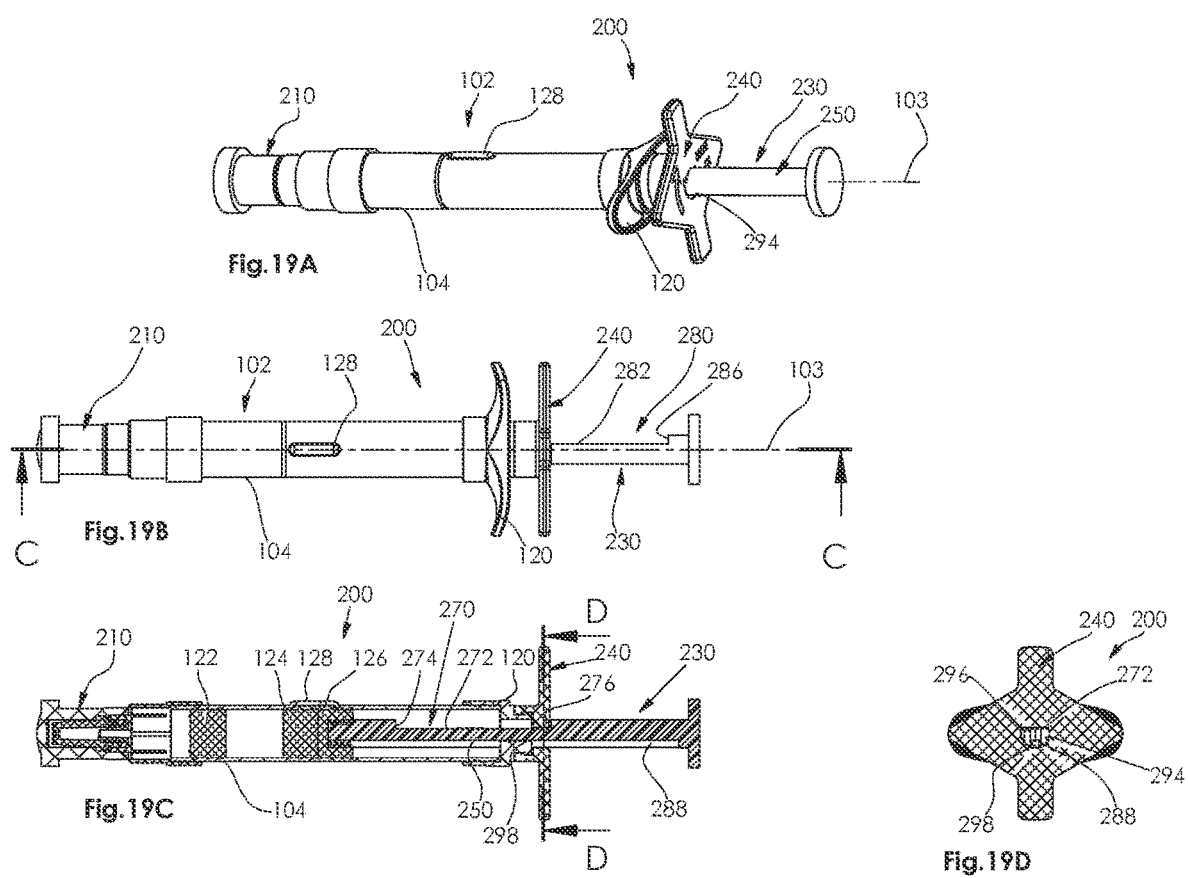

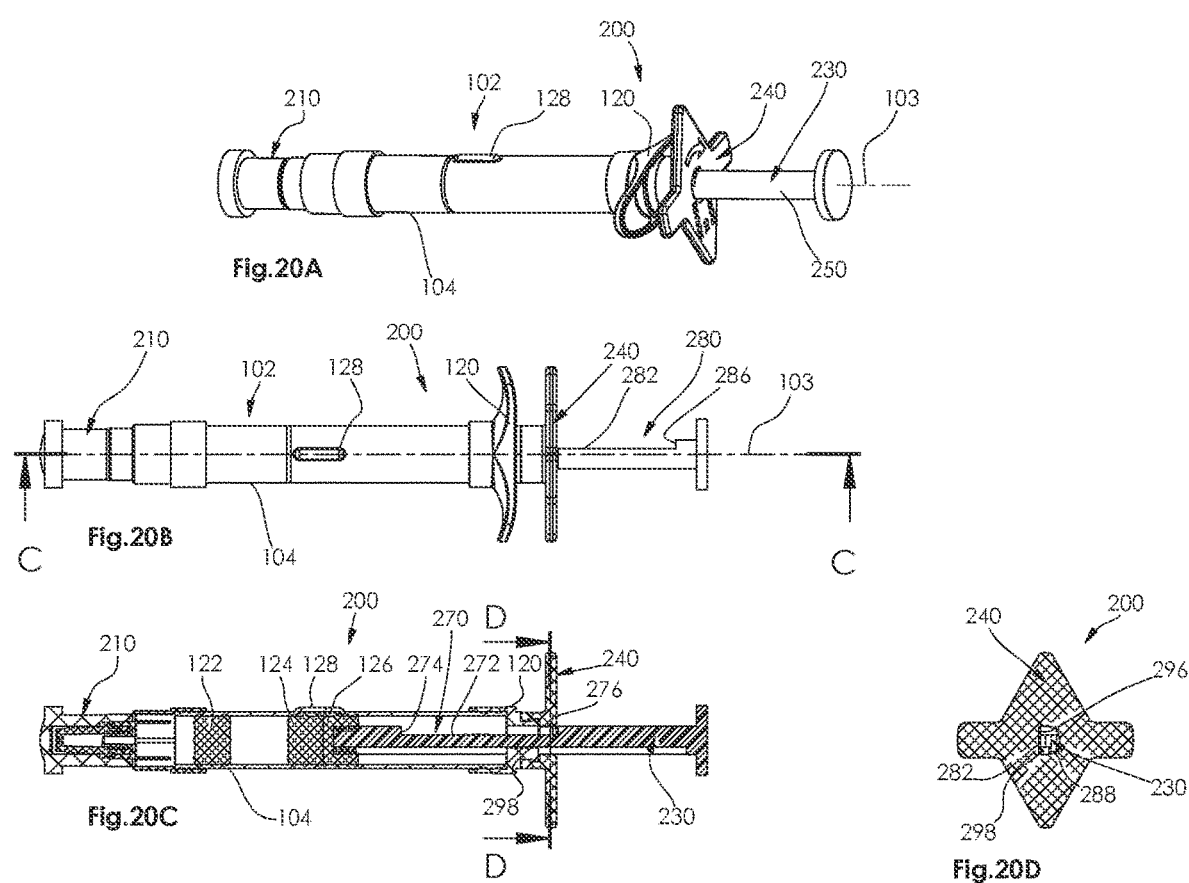

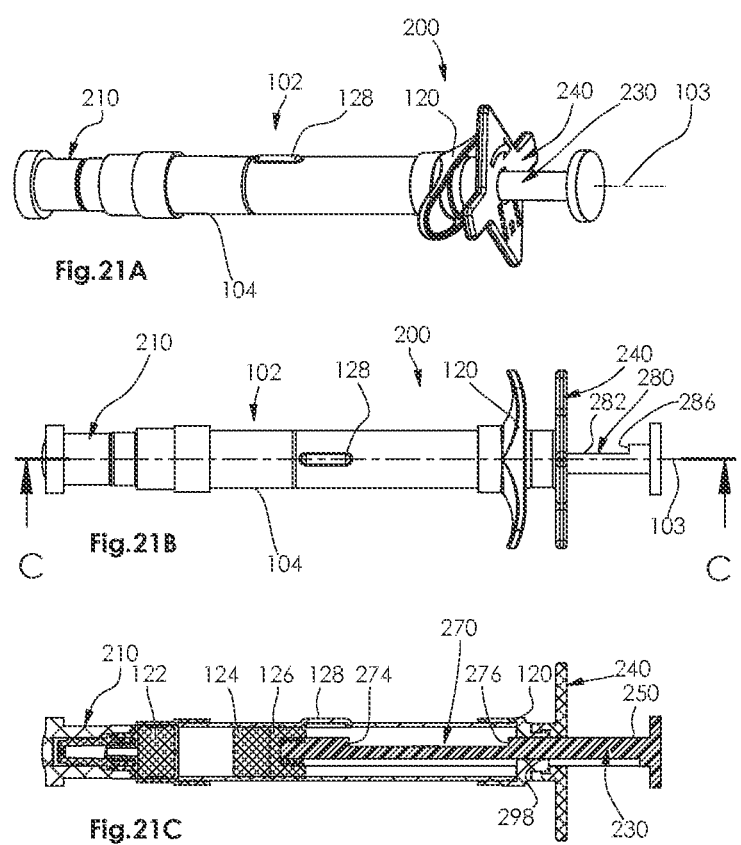

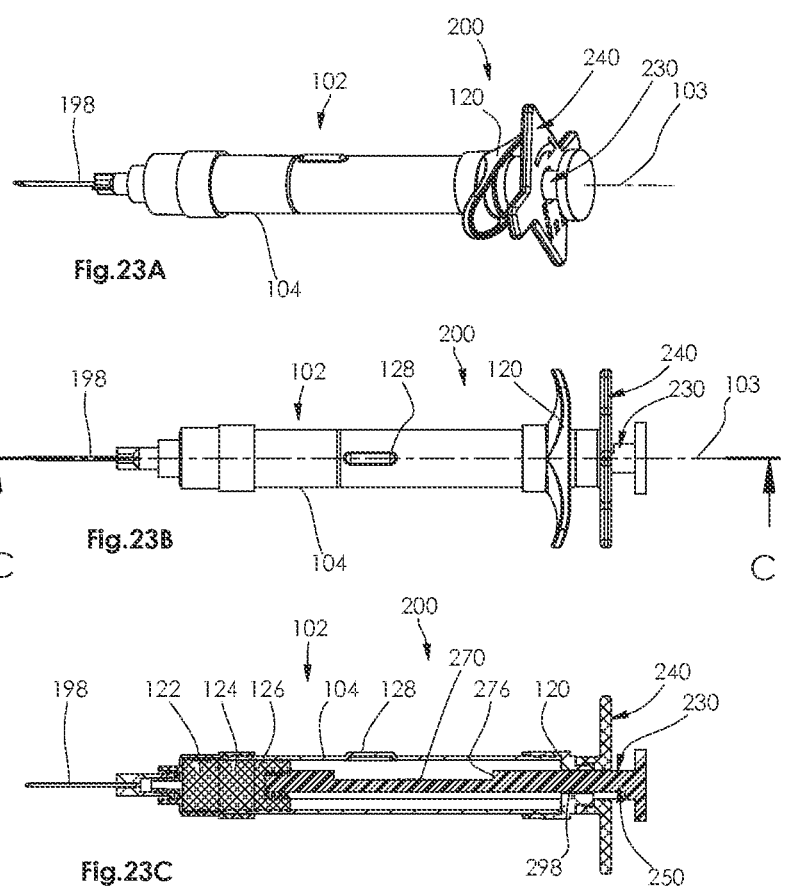

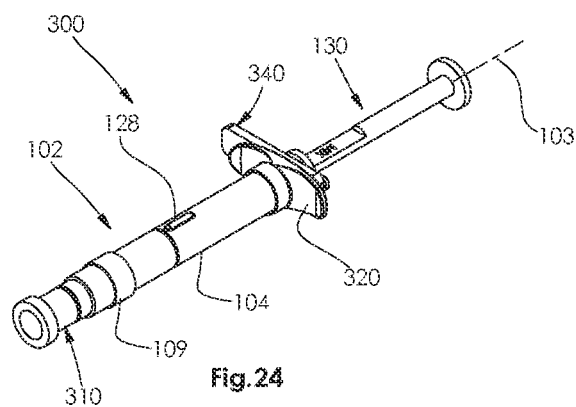
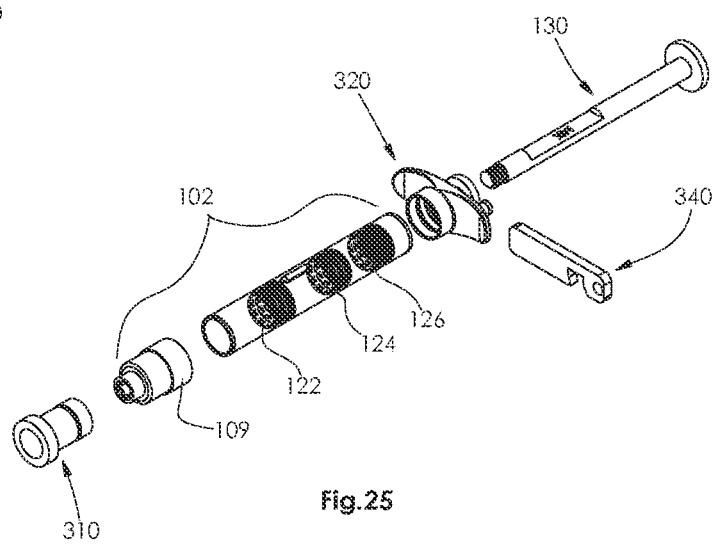

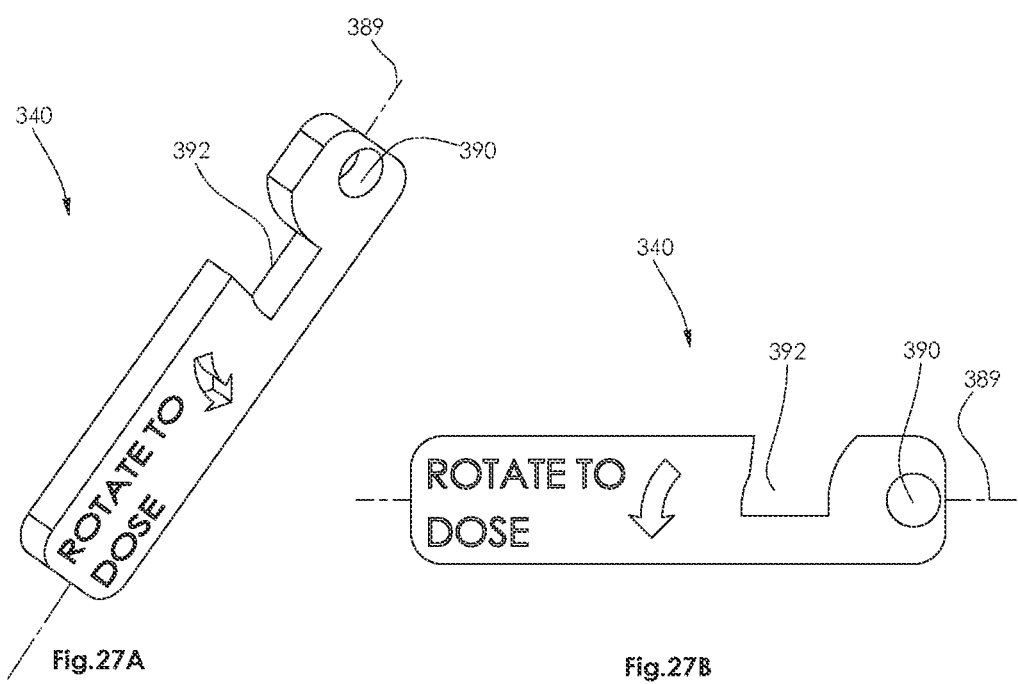

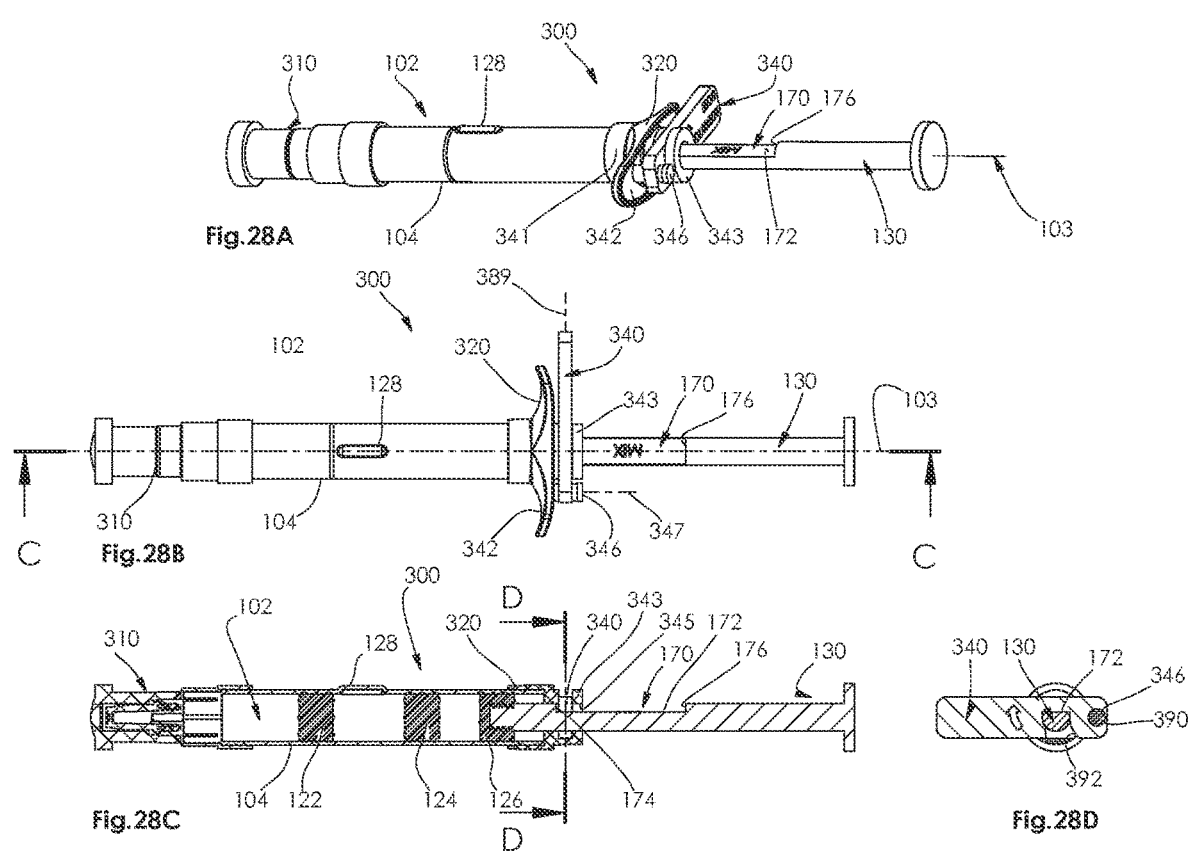

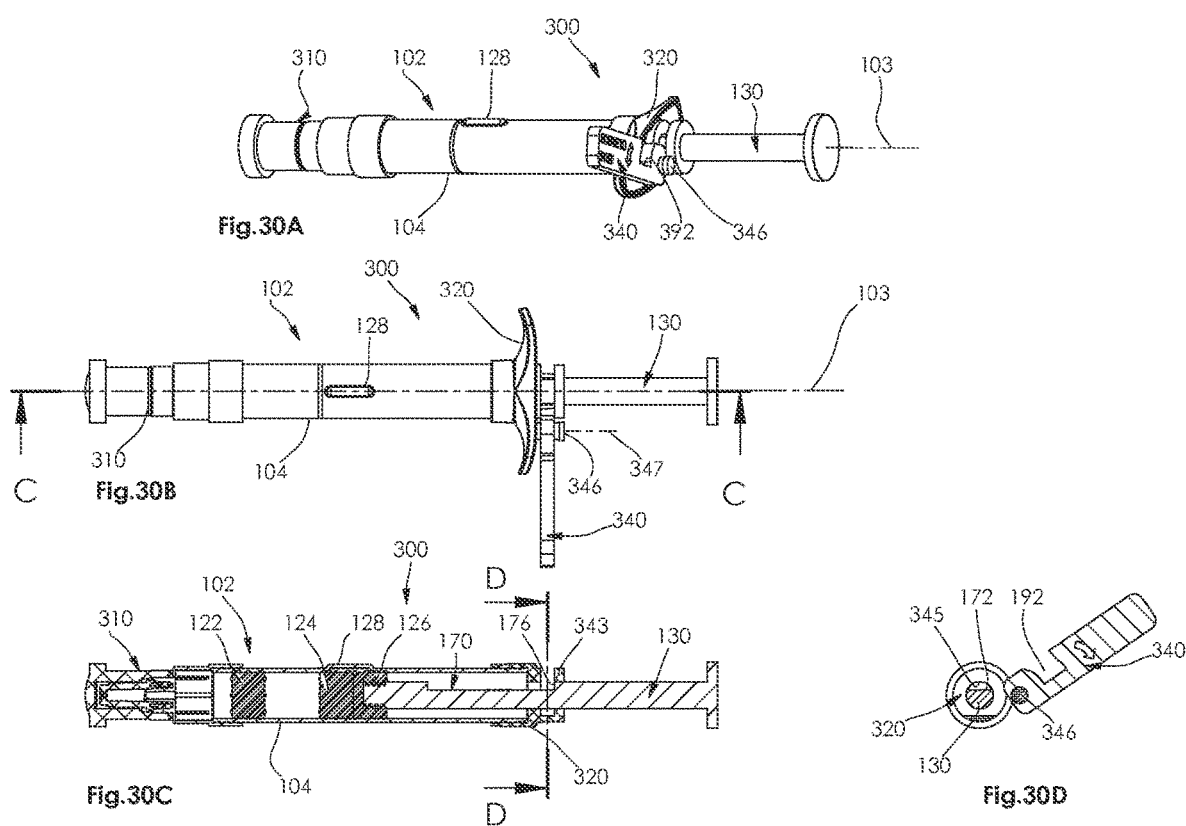

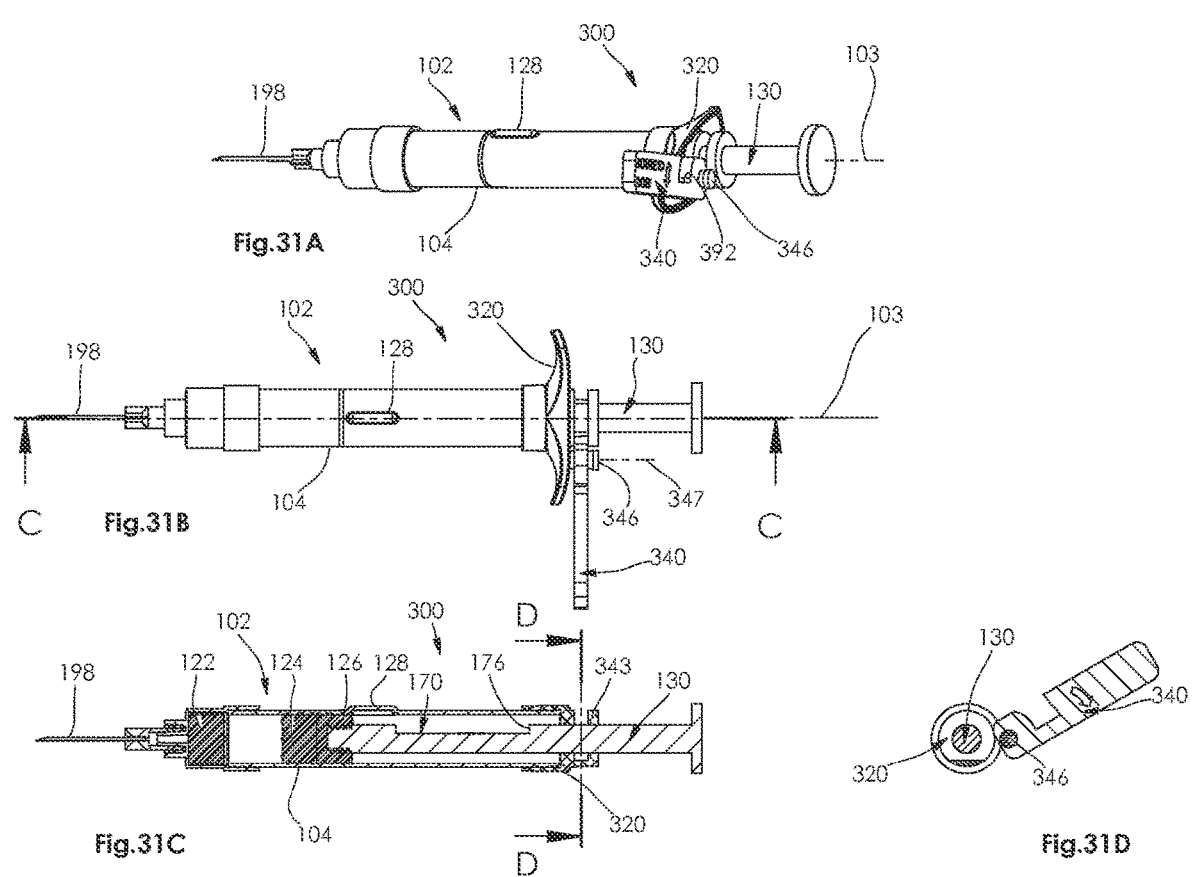

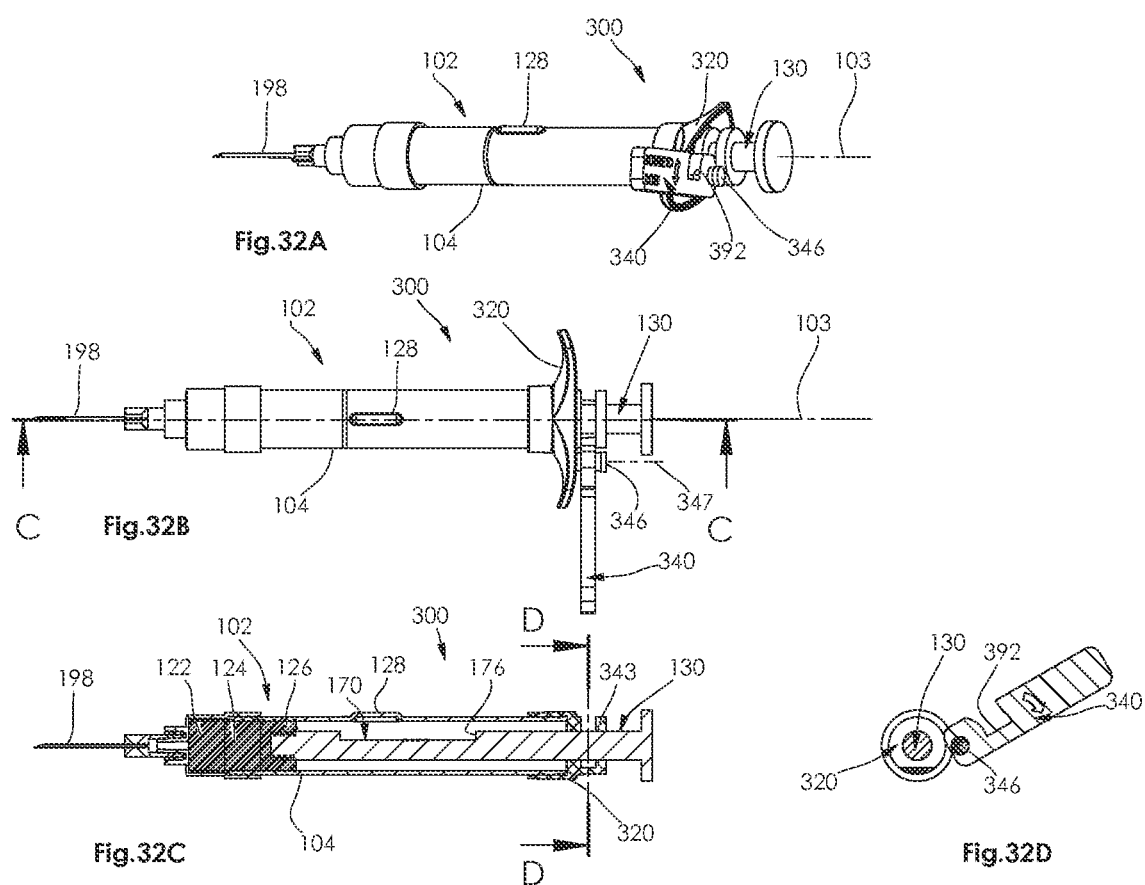

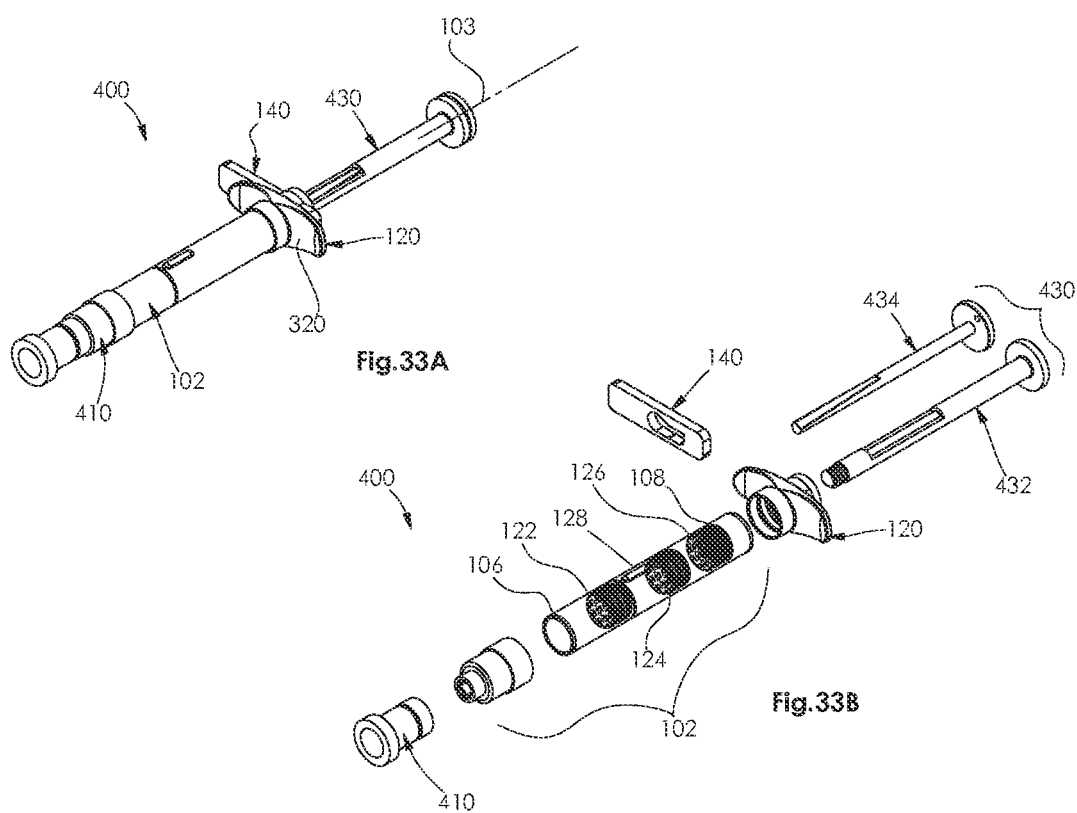

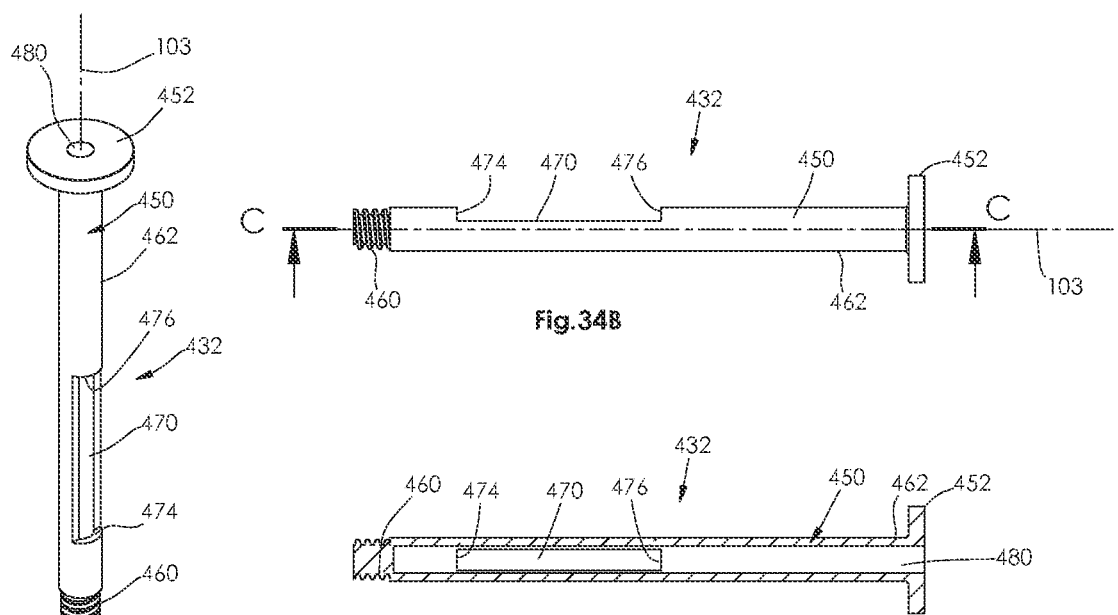

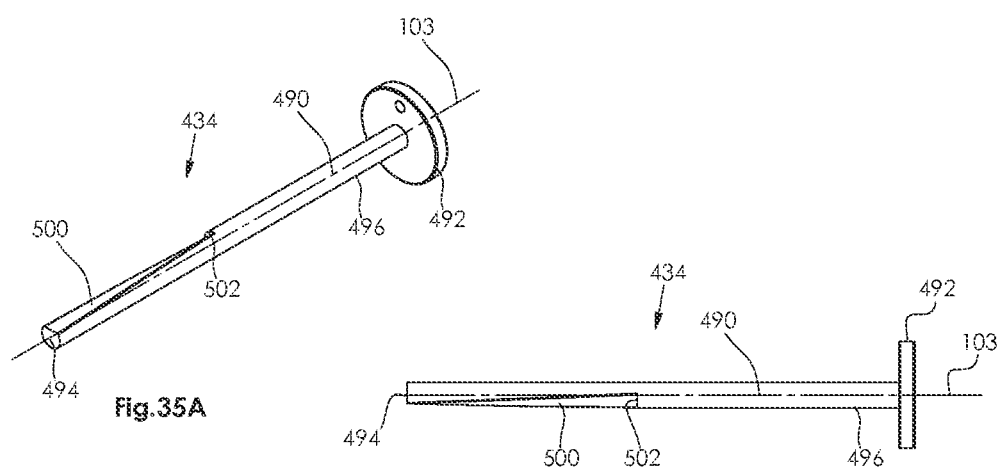
Fig.35A
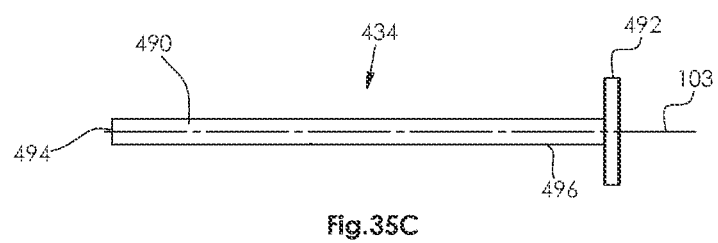
Fig.35B
Fig.35C

DUAL CHAMBER SYRINGE WITH A RESTRICTING ELEMENT AND METHODS OF USE THEREOF

REFERENCE TO RELATED APPLICATIONS

Reference is hereby made to PCT Publication No. WO2017077537, published May 11, 2017 and entitled "Safety Needles and Methods of Use Thereof", the disclosure of which is hereby incorporated by reference in its entirety.

Reference is also hereby made to U.S. patent application Ser. No. 16/994,596, filed Aug. 16, 2020 and entitled "Dual Chamber Syringe and Methods of Use Thereof" and to U.S. Provisional Patent Application No. 62/911,383, filed Oct. 7, 2019 and entitled "Dual Chamber Injection System and Methods of Use Thereof", the disclosures of which are hereby incorporated by reference in their entirety.

Reference is hereby made to U.S. Provisional Patent Application 63/090,229, filed Oct. 11, 2020 and entitled "Dual Chamber Syringe with a restricting element and Methods of Use Thereof", the disclosure of which is incorporated by reference in its entirety and priority of which is hereby claimed pursuant to 37 CFR 1.78(a) (4) and (5)(i).

FIELD OF THE INVENTION

The present invention generally relates to a dual chamber syringe, and more specifically to a pre-fillable dual chamber syringe and methods of use thereof for mixing and injection of a medicament.

BACKGROUND OF THE INVENTION

Pre-fillable dual chamber syringes are known in the art for separately containing a powder/liquid medicament preparation and a solvent in different chambers of the syringe.

It is also known that pre-fillable dual chamber syringes preferably include a syringe barrel with several pistons, which are slidably sealingly disposed therewithin and divide the syringe barrel into several separate chambers, whereas one of the chambers contains a powder medicament and another contains a solvent. Alternatively, both chambers may include liquids that are stored separately and that shall be mixed only at the time of injection.

The pre-fillable dual chamber syringes also include a plunger rod, which is operative to engage one of the pistons. Upon displacement of the plunger rod relative to the syringe barrel, the pistons are advanced within the syringe barrel and permit mixing of the medicament by combining several substances using a bypass formed in the syringe barrel.

SUMMARY OF THE INVENTION

The present invention seeks to provide an improved syringe assembly.

There is thus provided in accordance with an embodiment of the present invention or a combination of embodiments thereof a syringe assembly, comprising a syringe barrel having a forward end and a rearward end and being arranged along a longitudinal axis; a restricting element, moveably supported onto a portion of the syringe assembly and positionable in one of an injection disabling position and an injection enabling position in different operative orientations of the syringe assembly; a plunger rod assembly displaceable within the syringe barrel and operatively coupled with the restricting element; the plunger rod assembly having a restricting feature adapted to cooperate with the restricting element, such that when the restricting element is in the injection disabling position, the plunger rod assembly is permitted to be displaced axially forwardly only up to a certain longitudinal extent relative to the syringe barrel and when the restricting element is in the injection enabling position, the plunger rod assembly is permitted to be further displaced axially forwardly relative to the syringe barrel.

Preferably, the restricting element is positioned in the injection enabling position in an end of medicament mixing operative orientation of the syringe assembly thereby permitting further axial displacement of the plunger rod assembly relative to the syringe barrel in order to permit ejection of a medicament from the syringe barrel.

Further preferably, the longitudinal extent of the restricting feature defines the length of the travel path of the plunger rod assembly relative to the syringe barrel during the medicament mixing operative orientation. Still further preferably, the syringe assembly further comprises a finger grip associated with the syringe barrel, and wherein the restricting element is supported by the finger grip.

In accordance with an embodiment of the present invention, in order to position the restricting element in the injection enabling position, the restricting element is displaced transversely relative to the longitudinal axis. Preferably, the restricting element has a guiding slot with a wide slot portion and a narrow slot portion, the narrow slot portion having at least one flat edge, whereas the flat edge is configured for engagement with the restricting feature of the plunger rod assembly up to the end of medicament mixing operative orientation. Further preferably, at least one protrusion extends radially inwardly between the wide slot portion and the narrow slot portion, whereas during transitioning of the restricting element from the injection disabling position to the injection enabling position, a user has to apply a certain force that is greater than a predetermined force threshold to enable the plunger rod assembly to snap over the at least one protrusion.

Alternatively, in accordance with another embodiment of the present invention, in order to position the restricting element in the injection enabling position, the restricting element is displaced rotatably about the longitudinal axis. Preferably, a first restricting feature is formed along a portion of the length of the plunger rod assembly and a second restricting feature is formed along another portion of the length of the plunger rod assembly and the first and second restricting features are facing different angular directions. Further preferably, the restricting element has a slot with a flat edge, whereas the flat edge is configured for engagement with the first restricting feature of said plunger rod assembly up to the end of medicament mixing operative orientation and the flat edge is configured for engagement with the second restricting feature of the plunger rod assembly up to an end of injection operative orientation.

Further alternatively, in accordance with still another embodiment of the present invention, the finger grip has a pivot axis for attaching the restricting element thereto. Preferably, the restricting element has a cut-out configured to be operatively engaged with the plunger rod assembly in the injection disabling position. Further preferably, the restricting element is pivoted about the pivot axis to position the restricting element in the injection enabling position and thereby disengage the restricting element from the plunger rod assembly.

Still further alternatively, the plunger rod assembly includes a plunger rod outer portion and a plunger rod inner portion, which is insertable into the plunger rod outer portion and is rotatable relative thereto. Preferably, the plunger rod outer portion has an opening formed on a circumference thereof and the plunger rod inner portion has a spiral surface formed on a circumference thereof, wherein the spiral surface communicates with the opening and is adapted to engage the restricting element. Further preferably, the restricting element has a slot with a flat edge, whereas the flat edge is configured for engagement with the spiral surface of the plunger rod inner portion up to the end of medicament mixing operative orientation, thus urges rotation of the plunger rod inner portion relative to the restricting element during medicament mixing, thereby controlling the medicament mixing speed.

In accordance with an embodiment of the present invention, a method for delivering at least one medicament to a subject, the method comprising: providing a syringe assembly, having a syringe barrel having a forward end and a rearward end and being arranged along a longitudinal axis; movably coupling a restricting element onto a portion of the syringe assembly; providing a plunger rod assembly displaceable within the syringe barrel and operatively coupled with the restricting element, the plunger rod assembly having a restricting feature adapted to cooperate with the restricting element; permitting axial forward displacement of the plunger rod assembly relative to the syringe barrel only up to a certain longitudinal extent in order to perform medicament mixing when said restricting element is in an injection disabling position; thereafter, permitting further axial forward displacement of the plunger rod assembly relative to the syringe barrel when the restricting element is in an injection enabling position, thereby delivering the at least one medicament to the subject.

Preferably, in order to position the restricting element in the injection enabling position, the restricting element is displaced transversely relative to the longitudinal axis. Alternatively, in order to position the restricting element in the injection enabling position, the restricting element is displaced rotatably about the longitudinal axis. Further alternatively, in order to position the restricting element in the injection disabling position, the restricting element is engaged with the plunger rod assembly and in order to position the restricting element in the injection enabling position, the restricting element is disengaged from the plunger rod assembly.

BRIEF DESCRIPTION OF THE DRAWINGS

The present invention will be understood and appreciated more fully from the following detailed description, taken in conjunction with the drawings in which:

FIG. 1 is a simplified pictorial view of an assembled dual chamber syringe constructed and operative in accordance with an embodiment of the present invention;

FIG. 2 is a simplified pictorial exploded view of the dual chamber syringe of FIG. 1;

FIGS. 3A, 3B, 3C and 3D are respectively a simplified perspective view, a simplified plan side view and two simplified sectional views taken along orthogonal lines C-C in FIG. 3B and D-D in FIG. 3C of a syringe assembly forming part of the dual chamber syringe of FIGS. 1 & 2;

FIGS. 6A, 6B, 6C and 6D are simplified drawings of the dual chamber syringe of FIGS. 1-5B in a storage operative orientation, including respectively a simplified plan side view and three simplified sectional views taken along lines B-B in FIG. 6A and orthogonal lines C-C and D-D in FIG. 6B;

FIGS. 8A, 8B, 8C and 8D are simplified drawings of the dual chamber syringe of FIGS. 1-5B in a medicament mixing operative orientation, including respectively a simplified plan side view and three simplified sectional views taken along lines B-B in FIG. 8A and orthogonal lines C-C and D-D in FIG. 8B;

FIGS. 9A, 9B, 9C and 9D are simplified drawings of the dual chamber syringe of FIGS. 1-5B in an end of medicament mixing operative orientation, including respectively a simplified plan side view and three simplified sectional views taken along lines B-B in FIG. 9A and orthogonal lines C-C and D-D in FIG. 9B;

FIG. 14 is a simplified pictorial view of an assembled dual chamber syringe constructed and operative in accordance with another embodiment of the present invention;

FIG. 15 is a simplified pictorial exploded view of the dual chamber syringe of FIG. 14;

FIGS. 16A, 16B, 16C and 16D are respectively a simplified perspective view, two simplified plan side views and a simplified sectional view taken along lines D-D in FIG. 16B of a plunger rod forming part of the dual chamber syringe of FIGS. 14 & 15;

FIGS. 18A, 18B, 18C and 18D are simplified drawings of the dual chamber syringe of FIGS. 14-17D in a storage operative orientation, including respectively a simplified pictorial view, a simplified plan side view and two simplified sectional views taken along lines C-C in FIG. 18B and lines D-D in FIG. 18C;

FIGS. 19A, 19B, 19C and 19D are simplified drawings of the dual chamber syringe of FIGS. 14-17D in an end of medicament mixing operative orientation, including respectively a simplified pictorial view, a simplified plan side view and two simplified sectional views taken along lines C-C in FIG. 19B and lines D-D in FIG. 19C;

FIGS. 20A, 20B, 20C and 20D are simplified drawings of the dual chamber syringe of FIGS. 14-17D in an injection enablement operative orientation, including respectively a simplified pictorial view, a simplified plan side view and two simplified sectional views taken along lines C-C in FIG. 20B and lines D-D in FIG. 20C;

FIGS. 21A, 21B and 21C are simplified drawings of the dual chamber syringe of FIGS. 14-17D in a pre-injection operative orientation, including respectively a simplified pictorial view, a simplified plan side view and a simplified sectional view taken along lines C-C in FIG. 21B;

FIGS. 23A, 23B and 23C are simplified drawings of the dual chamber syringe of FIGS. 14-17D in an end of injection operative orientation, including respectively a simplified pictorial view, a simplified plan side view and a simplified sectional view taken along lines C-C in FIG. 23B;

FIG. 24 is a simplified pictorial view of an assembled dual chamber syringe constructed and operative in accordance with still another embodiment of the present invention;

FIG. 25 is a simplified pictorial exploded view of the dual chamber syringe of FIG. 24;

FIGS. 27A and 27B are respectively a simplified perspective view and a simplified plan side view of a restricting element forming part of the dual chamber syringe of FIGS. 24 & 25;

FIGS. 28A, 28B, 28C and 28D are simplified drawings of the dual chamber syringe of FIGS. 24-27B in a storage operative orientation, including respectively a simplified pictorial view, a simplified plan side view and two simplified sectional views taken along lines C-C in FIG. 28B and lines D-D in FIG. 28C;

FIGS. 30A, 30B, 30C and 30D are simplified drawings of the dual chamber syringe of FIGS. 24-27B in an injection enablement operative orientation, including respectively a simplified pictorial view, a simplified plan side view and two simplified sectional views taken along lines C-C in FIG. 30B and lines D-D in FIG. 30C;

FIGS. 31A, 31B, 31C and 31D are simplified drawings of the dual chamber syringe of FIGS. 24-27B in a needle attachment operative orientation, including respectively a simplified pictorial view, a simplified plan side view and two simplified sectional views taken along lines C-C in FIG. 31B and lines D-D in FIG. 31C;

FIGS. 32A, 32B, 32C and 32D are simplified drawings of the dual chamber syringe of FIGS. 24-27B in an end of injection operative orientation, including respectively a simplified pictorial view, a simplified plan side view and two simplified sectional views taken along lines C-C in FIG. 32B and lines D-D in FIG. 32C;

FIG. 33A is a simplified pictorial view of an assembled dual chamber syringe constructed and operative in accordance with yet another embodiment of the present invention;

FIG. 33B is a simplified pictorial exploded view of the dual chamber syringe of FIG. 33A;

FIGS. 34A, 34B and 34C are respectively a simplified perspective view, a simplified plan side view and a simplified sectional view taken along lines C-C in FIG. 34B of an outer portion of a plunger rod forming part of the dual chamber syringe of FIGS. 33A & 33B;

FIGS. 35A, 35B and 35C are respectively a simplified perspective view and two simplified plan side views of an inner portion of a plunger rod forming part of the dual chamber syringe of FIGS. 33A & 33B;

DESCRIPTION OF EMBODIMENTS

Figure 4A:
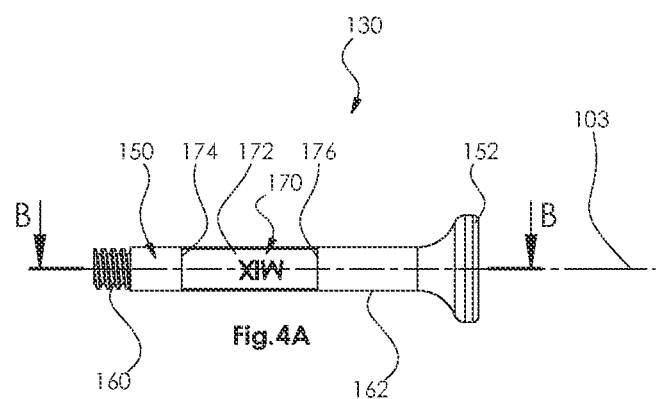
FIGS. 4A and 4B are respectively a simplified plan side view and a simplified sectional view taken along lines B-B in FIG. 4A of a plunger rod forming part of the dual chamber syringe of FIGS. 1 & 2.

The principles, uses and implementations of the teachings herein may be better understood with reference to the accompanying description and figures. Upon perusal of the description and figures present herein, one skilled in the art is able to implement the invention without undue effort or experimentation.

Before explaining at least one embodiment of the invention in detail, it is to be understood that the invention is not limited in its applications to the details of construction and the arrangement of the components and/or methods set forth in the following description and/or illustrated in the drawings and/or the Examples. The invention can be implemented with other embodiments and can be practiced or carried out in various ways. It is also understood that the phraseology and terminology employed herein is for descriptive purpose and should not be regarded as limiting.

Some embodiments of the invention are described herein with reference to the accompanying figures. The description, together with the figures, makes apparent to a person having ordinary skill in the art how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

Reference is now made to FIG. 1, which is a simplified pictorial view of an assembled dual chamber syringe constructed and operative in accordance with an embodiment of the present invention and to FIG. 2, which is a simplified pictorial exploded view of the dual chamber syringe of FIG. 1.

As seen in FIGS. 1 and 2, a dual chamber syringe 100 preferably includes a syringe assembly 102 arranged along a longitudinal axis 103. The syringe assembly 102 has a syringe barrel 104 having a forward end 106 and a rearward end 108 and a needle protection assembly 110, which is preferably fixedly connected to the proximal end 106 of the syringe barrel 104. It is appreciated that the needle protection assembly 110 is substantially similar to that described in PCT Publication No. WO2017077537, the disclosure of which is hereby incorporated by reference in its entirety. It is further appreciated that the syringe assembly 102 is substantially similar to that described in U.S. patent application Ser. No. 16/994,596, the disclosure of which is hereby incorporated by reference in its entirety.

It is also seen in FIGS. 1 & 2 that a finger grip 120 is fixedly connected or integrally made with the rearward end 108 of the syringe barrel 104. The syringe assembly 102 also preferably includes two chambers and two pistons, namely a forward piston 124, and a rearward piston 126, which are contained within the syringe barrel 104 and are adapted for slidable axial displacement relative to the syringe barrel 104. It is appreciated that a first chamber contains a first substance that can be a powder medicament, which is preferably confined between the forward piston 124 and the forward end 106 of the syringe barrel 104 and the second chamber contains a second substance, which can be a solvent, which is preferably confined between the forward piston 124 and the rearward piston 126 and upon appropriate longitudinal displacement of the pistons, the two substances are configured for mixing and subsequent ejection, as described in detail hereinbelow.

Alternatively, a first liquid medicament can be confined between the forward piston 124 and the forward end 106 of the syringe barrel 104 and a second liquid medicament can be confined between the forward piston 124 and the rearward piston 126 and upon appropriate longitudinal displacement of the pistons, the two substances are configured for mixing and subsequent ejection. It is noted that the first liquid medicament can alternatively be confined between a pair of pistons and the second liquid medicament can be confined between another pair of pistons.

Further alternatively, more than two chambers can be provided within the syringe barrel, divided by more than one piston, and thus more than two substances can be mixed during various mixing stages before the injection of medication can take place.

The syringe barrel 104 is preferably made of glass and can alternatively be made of plastic or any other suitable material. The syringe barrel has a generally cylindrical shape and extends along the longitudinal axis 103. A bypass protrusion 128 is disposed generally at an intermediate location of the syringe barrel 104 along axis 103. The bypass protrusion 128 generally extends radially outwardly from an outer surface of the syringe barrel 104 to facilitate fluid passage between the two chambers formed within the syringe barrel 104 between each pair of pistons.

It is noted that a plurality of bypass protrusions, such as bypass protrusion 128, may be formed on the syringe barrel 104, being longitudinally spaced from each other along axis 103 in order to facilitate mixing of more than two substances.

It is appreciated that syringe assembly 102 can be any type of conventional container, such as a cartridge commercially available from Schott Pharmaceutical Systems, Mainz, Germany or Vetter Pharma International USA Inc., IL, USA or Nuova Ompi S.r.l., Padua, Italy or may be any other suitable syringe or cartridge.

A plunger rod 130 is arranged along the longitudinal axis 103 and is adapted to be slidably received within the syringe barrel 104 and to be operatively associated with the finger grip 120. A restricting element 140 is configured to be moveably coupled to the syringe assembly 102 and operatively coupled with the plunger rod 130.

It is a particular feature of an embodiment of the present invention that the restricting element 140 restricts displacement of the plunger rod 130 relative to the syringe barrel 104 in certain operative orientations and enables displacement of the plunger rod 130 relative to the syringe barrel 104 in other operative orientations.

Reference is now made to FIGS. 3A, 3B, 3C and 3D, which are respectively a simplified perspective view, a simplified plan side view and two simplified sectional views taken along orthogonal lines C-C in FIG. 3B and D-D in FIG. 3C of the syringe assembly 102 forming part of the dual chamber syringe 100 of FIGS. 1 & 2.

It is seen in FIGS. 3A-3D and noted hereinabove that the syringe assembly 102 is substantially similar to that described in U.S. patent application Ser. No. 16/994,596, the disclosure of which is hereby incorporated by reference in its entirety.

The finger grip 120 preferably includes a flange-like rearward portion 142, which is rearwardly spaced from the rearward end 108 of the syringe barrel 104 and connected thereto by connecting wall 144. A through bore 146 is preferably formed within the rearward portion 142. Finger gripping protrusions 148 preferably extend radially outwardly from the syringe barrel 104 and are preferably forwardly spaced from rearward portion 142.

A particular feature of an embodiment of the present invention is that at least two bypass protrusions 128 are formed on the circumference of the syringe barrel 104, thus facilitating control of the force the user has to apply in order to perform mixing of the medicament contained within the barrel assembly 102. The required force decreases inherently once a plurality of bypass protrusions are formed on the syringe barrel 104, thus increasing the surface area communicating with the fluid.

Figure 4B:
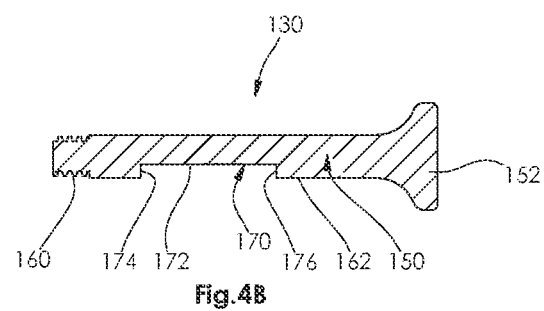

Reference is now made to FIGS. 4A and 4B, which are respectively a simplified plan side view and a simplified sectional view taken along lines B-B in FIG. 4A of the plunger rod 130 forming part of the dual chamber syringe 100 of FIGS. 1 & 2.

The plunger rod 130 preferably is an integrally formed element, preferably injection molded of plastic and is arranged along longitudinal axis of symmetry 103.

The plunger rod 130 preferably includes a longitudinal shaft 150 terminating at a generally circular flange 152 at a rearward end thereof. The circular flange 152 extends generally radially outwardly from the outer surface of the longitudinal shaft 150 and is disposed generally transversely with respect thereto. An externally threaded protrusion 160 preferably extends forwardly from a forward end of the longitudinal shaft 150. The longitudinal shaft 150 is preferably generally cylindrical, defining an outer circumferential surface 162.

It is a particular feature of an embodiment of the present invention that a restricting feature, such as cut-out 170 is formed along a portion of the length of the longitudinal shaft 150. The cut-out 170 extends generally radially inwardly from circumferential surface 162 and defines a flat wall 172, which is disposed radially inwardly of the circumferential surface 162 and two mutually opposed shoulders generally bounding the flat wall 172, a rearwardly facing shoulder 174 and a forwardly facing surface 176. It is appreciated that any alternative shape of cut-out 170 that is adapted for operatively engaging the restricting element 140 and prevent further forward advancement of the plunger rod 130 along the longitudinal axis 103 is within the scope of the embodiments of the present invention.

It is noted that an indication for the medicament mixing operative orientation is provided on the flat wall 172 of the plunger rod 130. The indication may be provided in form of text, illustration, color or any other form of visual indication.

It is a particular feature of an embodiment of the present invention that the length of the restricting feature, according to this embodiment the length of the flat wall 172, defines the length of the travel path of the plunger rod 130 relative to the syringe barrel 104 during the medicament mixing operative orientation.

Figure 5A:
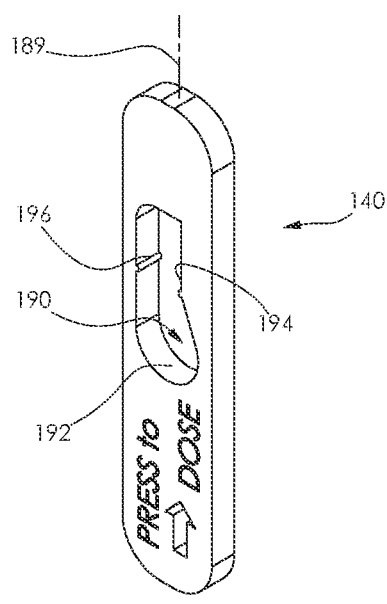
FIGS. 5A and 5B are respectively a simplified pictorial view and a simplified plan side view of a restricting element forming part of the dual chamber syringe of FIGS. 1 & 2.
Figure 5B:
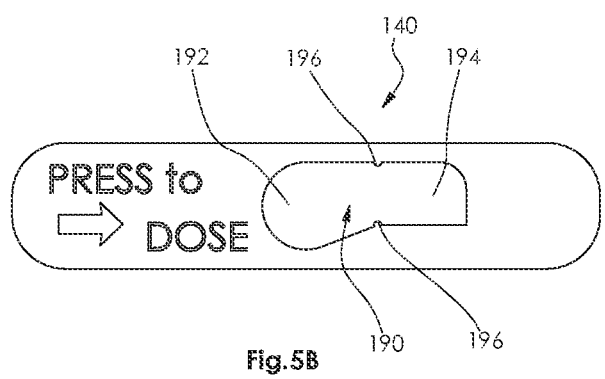

Reference is now made to FIGS. 5A and 5B, which are respectively a simplified pictorial view and a simplified plan side view of the restricting element 140 forming part of the dual chamber syringe 100 of FIGS. 1 & 2.

The restricting element 140 preferably is an integrally formed flange-like preferably flat longitudinal element arranged along longitudinal axis 189.

A two-portion guiding slot 190 is formed in the restricting element 140. The two-portion guiding slot 190 preferably includes a relatively widened slot portion 192, having at least one circular segment and a relatively narrow slot portion 194, having at least one flat edge. Preferably, slightly inwardly extending protrusions 196 are formed between the widened slot portion 192 and a narrow slot portion 194.

A visual indication showing the intended displacement direction of the restricting element 140 is preferably provided thereon.

Reference is now made to FIGS. 6A, 6B, 6C and 6D, which are simplified drawings of the dual chamber syringe 100 of FIGS. 1-5B in a storage operative orientation, including respectively a simplified plan side view and three simplified sectional views taken along lines B-B in FIG. 6A and orthogonal lines C-C and D-D in FIG. 6B.

It is seen in FIGS. 6A-6D that the dual chamber syringe 100 is arranged along the longitudinal axis 103.

The needle protection assembly 110 is preferably fixedly attached to the forward end 106 of the syringe barrel 104 and is adapted to seal a needle 198. The plunger rod 130 is partially slidably inserted into the syringe barrel 104 through bore 146 formed in the finger grip 120 and engages the rearward piston 126.

It is a particular feature of an embodiment of the present invention that the restricting element 140 is operatively engaged with the plunger rod 130 and is supported between the gripping protrusions 148 and between the rearward portion 142 of the finger grip 120.

It is noted that the restricting element 140 is arranged along axis 189, which preferably extends generally transversely to longitudinal axis 103.

It is particularly seen in FIGS. 6C and 6D that in this storage operative orientation the plunger rod 130 is disposed in the narrow portion 194 of the restricting element 140, thus the narrow portion 194 engages the flat wall 172 of the cut-out 170 of the plunger rod 130. In this storage operative orientation, before medicament mixing is initiated, the restricting element 140 is disposed adjacent the forward end of the cut-out 170 and is preferably supported against rearwardly facing shoulder 174 of the plunger rod 130, as specifically seen in FIG. 6B.

It is additionally seen in FIGS. 6B and 6C that the forward piston 124 is sealingly slidably disposed with respect to the inner surface of the syringe barrel 104 and is located generally between the rearward end 108 of the syringe barrel 104 and between the bypass protrusion 128.

It is noted that a first substance is confined between the forward end 106 of the syringe barrel 104 and the forward piston 124 and a second substance is confined between the forward piston 124 and the rearward piston 126.

Figure 7A:
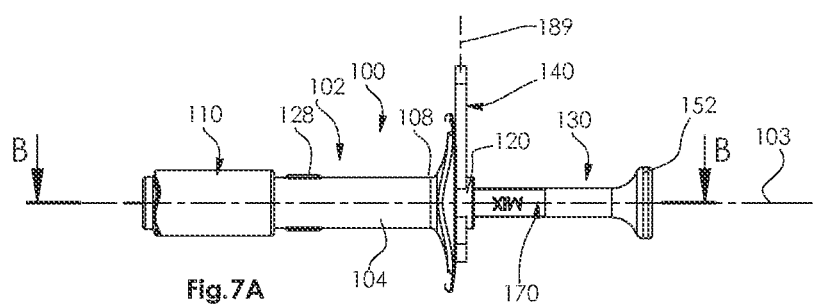
FIGS. 7A, 7B, 7C and 7D are simplified drawings of the dual chamber syringe of FIGS. 1-5B in a pre-mixing operative orientation, including respectively a simplified plan side view and three simplified sectional views taken along lines B-B in FIG. 7A and orthogonal lines C-C and D-D in FIG. 7B.
Figure 7B:
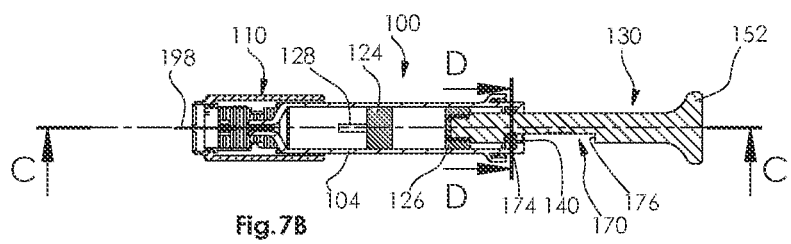
Figure 7D:
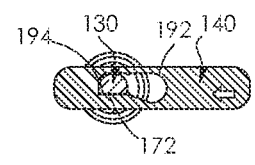
Figure 7C:
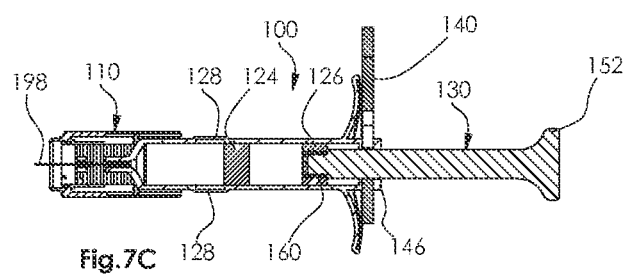

Reference is now made to FIGS. 7A, 7B, 7C and 7D, which are simplified drawings of the dual chamber syringe 100 of FIGS. 1-5B in a pre-mixing operative orientation, including respectively a simplified plan side view and three simplified sectional views taken along lines B-B in FIG. 7A and orthogonal lines C-C and D-D in FIG. 7B.

It is noted that all spatial relationships between the various components of the dual chamber syringe 100 remain essentially the same as described hereinabove with respect to the storage operative orientation, besides that the needle 198 is now exposed by removing a needle cover, forming part of the needle protection assembly 110.

Reference is now made to FIGS. 8A, 8B, 8C and 8D, which are simplified drawings of the dual chamber syringe 100 of FIGS. 1-5B in a medicament mixing operative orientation, including respectively a simplified plan side view and three simplified sectional views taken along lines B-B in FIG. 8A and orthogonal lines C-C and D-D in FIG. 8B.

It is noted that all spatial relationships between the various components of the dual chamber syringe 100 remain essentially the same as described hereinabove with respect to the pre-mixing operative orientation, besides the following:

The plunger rod 130 is advanced forwardly relative to the syringe barrel 104 along longitudinal axis 103, whereas the narrow portion 194 of the restricting element 140 is guided along the flat wall 172 of the plunger rod 130 in this operative orientation. It is seen that the rearwardly facing shoulder 174 of the plunger rod 130 is now forwardly spaced from the restricting element 140.

It is also seen in FIGS. 8A-8D that the rearward piston 126 is forwardly axially displaced relative to the syringe barrel 104 along with the plunger rod 130, due to the threadable engagement therebetween. The forward piston 124 is correspondingly axially forwardly displaced relative to the syringe barrel 104 due to the hydraulic pressure created in the syringe chamber containing the second substance and in the syringe chamber containing the first substance. It is noted that in this medicament mixing operative orientation, the forward piston 124 is generally aligned with the bypass protrusions 128 of the syringe barrel 104.

Reference is now made to FIGS. 9A, 9B, 9C and 9D, which are simplified drawings of the dual chamber syringe 100 of FIGS. 1-5B in an end of medicament mixing operative orientation, including respectively a simplified plan side view and three simplified sectional views taken along lines B-B in FIG. 9A and orthogonal lines C-C and D-D in FIG. 9B.

It is seen in FIGS. 9A-9D that the plunger rod 130 is further axially forwardly advanced relative to the syringe barrel 104 along longitudinal axis 103 whereas the narrow portion 194 of the restricting element 140 is further guided along the flat wall 172 of the plunger rod 130 in this operative orientation.

It is a particular feature of an embodiment of the present invention that the plunger rod 130 is operatively coupled with the restricting element 140, whereas the cut-out 170 of the plunger rod 130 is adapted to cooperate with the restricting element 140 such that upon positioning of the restricting element 140 in an injection disabling position, the plunger rod 130 is permitted to be displaced longitudinally axially forwardly only up to a certain longitudinal extent and upon positioning of the restricting element 140 in an injection enabling position, the plunger rod 130 is permitted to be further displaced longitudinally axially forwardly along longitudinal axis 103.

Specifically, at the end of medicament mixing, the forwardly facing shoulder 176 of the plunger rod 130 engages the restricting element 140, thus preventing further forward axial displacement of the plunger rod 130. It is thus appreciated that once medicament mixing is completed, the plunger rod 130 is prevented from initiating injection of the diluted medicament by means of operative engagement of the plunger rod 130 and the restricting element 140, namely by engagement between the narrow portion 194 of the restricting element 140 and the cut-out 170 of the plunger rod 130.

It is a particular feature of an embodiment of the present invention that, as seen in FIGS. 9A-9D, the dual-chamber syringe 100 is disposed in end of medicament mixing operative orientation and the restricting element 140 is disposed in the injection disabling position, thus preventing further forward axial displacement of the plunger rod 130 relative to the syringe barrel 104.

During the medicament mixing, one of the substances contained in a first chamber passes into another chamber containing another substance through at least one of the bypass protrusions 128 of the syringe barrel 104 in order to mix the substances resulting in a liquid medicament solution now contained between the forward end 106 of the syringe barrel 104 and the forward piston 124.

It is seen that in the end of medicament mixing, as shown in FIGS. 9A-9D, the entire amount of the first substance passed into the chamber containing the second substance and created liquid medicament solution.

It is noted that alternatively more than two chambers can be provided within the syringe barrel 104, divided by more than one piston, and thus more than two substances can be mixed using several longitudinally spaced bypass protrusions 128 during various mixing stages before the injection of medication can take place.

Figure 10A:
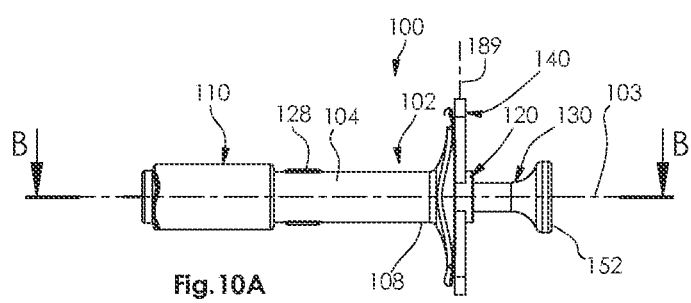
FIGS. 10A, 10B, 10C and 10D are simplified drawings of the dual chamber syringe of FIGS. 1-5B in an injection enablement operative orientation, including respectively a simplified plan side view and three simplified sectional views taken along lines B-B in FIG. 10A and orthogonal lines C-C and D-D in FIG. 10B.
Figure 10B:
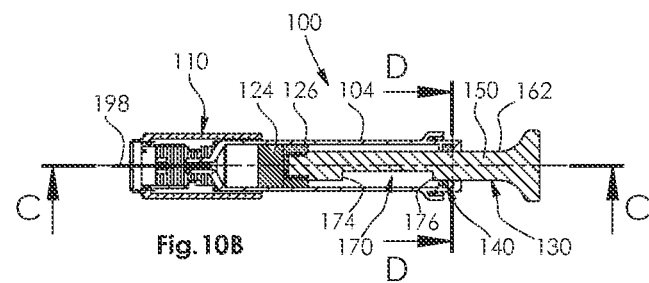

Reference is now made to FIGS. 10A, 10B, 10C and 10D, which are simplified drawings of the dual chamber syringe 100 of FIGS. 1-5B in an injection enablement operative orientation, including respectively a simplified plan side view and three simplified sectional views taken along lines B-B in FIG. 10A and orthogonal lines C-C and D-D in FIG. 10B.

It is a particular feature of an embodiment of the present invention that the restricting element 140 is transitioned into the injection enabling position in order to permit further forward displacement of the plunger rod 130 relative to the syringe barrel 104 and thereby facilitate ejection of the liquid medicament solution from the syringe barrel through the needle 198.

It is a further particular feature of an embodiment of the present invention that in order to transition the restricting element 140 into the injection enabling position, the restricting element 140 is displaced axially along axis 189, so that the wider portion 192 of the restricting element 140 is now associated with the longitudinal shaft 150 of the plunger rod 130. It is appreciated that the restricting element 140 is displaced transversely relative to the syringe assembly 102 and relative to the plunger rod 130.

Figure 10D:
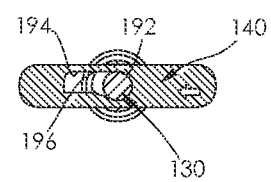
Figure 10C:
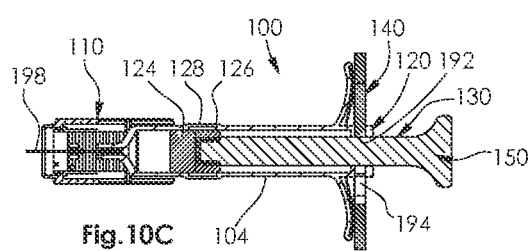

Following the transition of the restricting element 140 into the injection enabling position, the longitudinal shaft 150 of the plunger rod 130 is guided longitudinally forwardly through the wider portion 192 of the restricting element 140, thus the wider portion 192 of the restricting element 140 now engages the outer circumferential surface 162 of the plunger rod 130, rearwardly of the cut-out 170, between the rearward end 108 of the syringe barrel 104 and the flange 152 of the plunger rod 130, as specifically seen in FIGS. 10B & 10D.

It is a further particular feature of an embodiment of the present invention that during the transitioning of the restricting element 140 from the injection disabling position to the injection enabling position, the user has to apply a certain force that is greater than a predetermined force threshold to enable the protrusion 196 of the restricting element 140 to snap over the plunger rod 130.

Figure 11A:
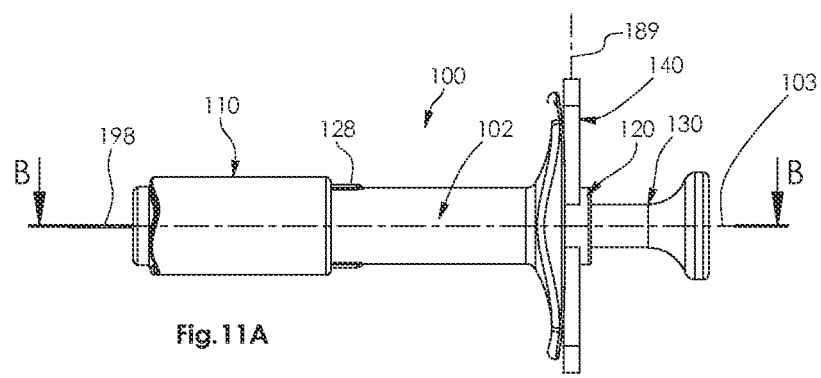
FIGS. 11A and 11B are simplified drawings of the dual chamber syringe of FIGS. 1-5B in a needle penetration operative orientation, including respectively a simplified plan side view and a simplified sectional view taken along lines B-B in FIG. 11A.
Figure 11B:
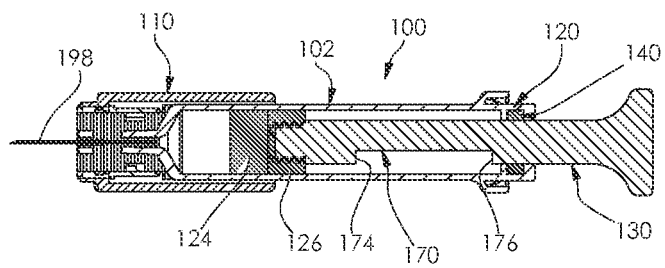

Reference is now made to FIGS. 11A and 11B, which are simplified drawings of the dual chamber syringe 100 of FIGS. 1-5B in a needle penetration operative orientation, including respectively a simplified plan side view and a simplified sectional view taken along lines B-B in FIG. 11A.

It is noted that all spatial relationships between the various components of the dual chamber syringe 100 remain essentially the same as described hereinabove with respect to the injection enablement operative orientation, besides that the dual chamber syringe 100 is now pressed against the skin and the needle 198 penetrates into the injection site.

Figure 12A:
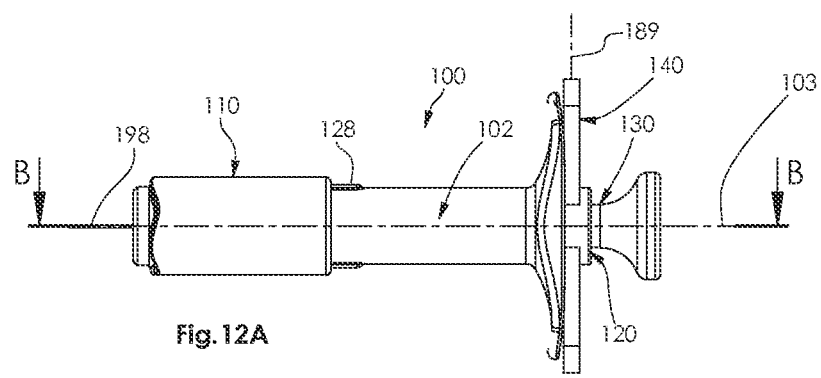
FIGS. 12A and 12B are simplified drawings of the dual chamber syringe of FIGS. 1-5B in an end of injection operative orientation, including respectively a simplified plan side view and a simplified sectional view taken along lines B-B in FIG. 12A.
Figure 12B:
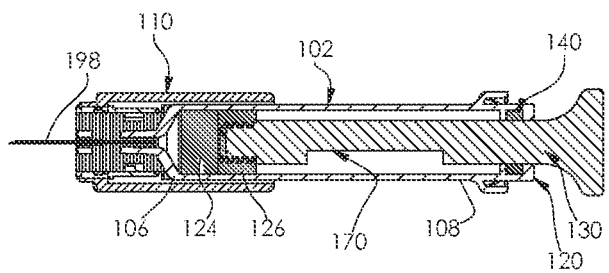

Reference is now made to FIGS. 12A and 12B, which are simplified drawings of the dual chamber syringe 100 of FIGS. 1-5B in an end of injection operative orientation, including respectively a simplified plan side view and a simplified sectional view taken along lines B-B in FIG. 12A.

It is noted that all spatial relationships between the various components of the dual chamber syringe 100 remain essentially the same as described hereinabove with respect to the needle penetration operative orientation, besides that the plunger rod 130 is further axially longitudinally forwardly displaced relative to the syringe barrel 104 to provide for passage of liquid medicament solution through the needle 198.

The dual chamber syringe 100 is shown at the end of injection in FIGS. 12A & 12B, whereas the entire amount of the liquid medicament solution passed through the needle 198. It is seen in FIG. 12B that the two pistons 124 and 126 are now disposed at their forwardmost position and abut each other, while all liquid medicament solution is ejected from the dual chamber syringe 100.

Figure 13A:
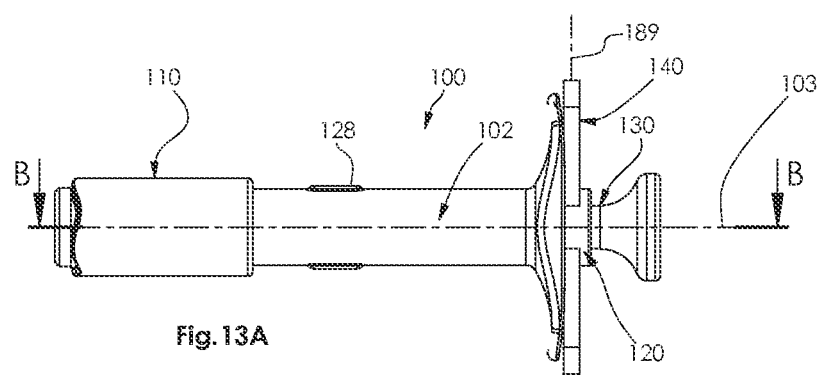
FIGS. 13A and 13B are simplified drawings of the dual chamber syringe of FIGS. 1-5B in a needle protection operative orientation, including respectively a simplified plan side view and a simplified sectional view taken along lines B-B in FIG. 13A.
Figure 13B:
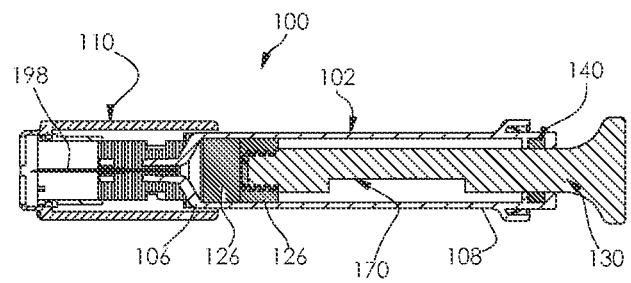

Reference is now made to FIGS. 13A and 13B, which are simplified drawings of the dual chamber syringe 100 of FIGS. 1-5B in a needle protection operative orientation, including respectively a simplified plan side view and a simplified sectional view taken along lines B-B in FIG. 13A.

It is noted that all spatial relationships between the various components of the dual chamber syringe 100 remain essentially the same as described hereinabove with respect to the end of injection operative orientation, besides that the needle protection assembly 110 is now displaced forwardly relative to the syringe barrel 104 and encloses the needle 198 therewithin.

Reference is now made to FIG. 14, which is a simplified pictorial view of an assembled dual chamber syringe constructed and operative in accordance with another embodiment of the present invention and to FIG. 15, which is a simplified pictorial exploded view of the dual chamber syringe of FIG. 14.

A dual chamber syringe 200 constructed and operative in accordance with another embodiment of the present invention is described and illustrated in FIGS. 14 & 15. Some of the elements of the dual chamber syringe 200 are similar or identical to the elements of dual chamber syringe 100, which is described with reference to FIGS. 1A-13B. Same elements are designated with same reference numerals.

As seen in FIGS. 14 and 15, a dual chamber syringe 200 preferably includes a syringe assembly 102 arranged along a longitudinal axis 103. The syringe assembly 102 has a syringe barrel 104 having a forward end 106 and a rearward end 108, a luer lock hub 109 preferably being fixedly attached to the forward end 106 of the syringe barrel and a cover 210. It is appreciated that the syringe assembly 102 is substantially similar to that described in U.S. patent application Ser. No. 16/994,596, the disclosure of which is hereby incorporated by reference in its entirety.

It is also seen in FIGS. 14 & 15 that a finger grip 120 is fixedly connected or integrally made with the rearward end 108 of the syringe barrel 104. The syringe assembly 102 also preferably includes three pistons, namely a forward piston 122, an intermediate piston 124 and a rearward piston 126, which are contained within the syringe barrel 104 and are adapted for slidable axial displacement relative to the syringe barrel 104. It is appreciated that a first substance is preferably confined between one pair of the pistons and a second substance is preferably confined between another pair of the pistons and upon appropriate longitudinal displacement of the pistons, the two substances are configured for mixing and subsequent ejection, as described in detail hereinbelow.

The syringe barrel 104 is preferably made of glass and may alternatively be made of plastic. The syringe barrel has a generally cylindrical shape and extends along the longitudinal axis 103. A bypass protrusion 128 is disposed generally at an intermediate location of the syringe barrel 104 along axis 103. The bypass protrusion 128 generally extends radially outwardly from an outer surface of the syringe barrel 104 to facilitate fluid passage between the two chambers formed within the syringe barrel 104 between each pair of pistons.

It is appreciated that syringe assembly 102 can be any type of conventional container, such as a cartridge commercially available from Schott Pharmaceutical Systems, Mainz, Germany or Vetter Pharma International USA Inc., IL, USA or Nuova Ompi S.r.l., Padua, Italy or may be any other suitable syringe or cartridge.

A plunger rod 230 is arranged along the longitudinal axis 103 and is adapted to be slidably received within the syringe barrel 104. A restricting element 240 is configured to be moveably coupled to the finger grip 120 and to be operatively associated with the plunger rod 230.

It is a particular feature of an embodiment of the present invention that the restricting element 240 restricts displacement of the plunger rod 230 relative to the syringe barrel 104 in certain operative orientations and enables displacement of the plunger rod 230 relative to the syringe barrel 104 in other operative orientations.

Reference is now made to FIGS. 16A, 16B, 16C and 16D, which are respectively a simplified perspective view, two simplified plan side views and a simplified sectional view taken along lines D-D in FIG. 16B of the plunger rod 230 forming part of the dual chamber syringe 200 of FIGS. 14 & 15.

The plunger rod 230 preferably is an integrally formed element, preferably injection molded of plastic and is arranged along longitudinal axis of symmetry 103.

The plunger rod 230 preferably includes a longitudinal shaft 250 terminating at a generally circular flange 252 at a rearward end thereof. The circular flange 252 extends generally radially outwardly from the outer surface of the longitudinal shaft 250 and is disposed generally transversely with respect thereto. An externally threaded protrusion 260 extends forwardly from a forward end of the longitudinal shaft 250. The longitudinal shaft 250 is preferably generally cylindrical, defining an outer circumferential surface 262.

It is a particular feature of an embodiment of the present invention that a first cut-out 270 is formed along a portion of the length of the longitudinal shaft 250. The first cut-out 270 is disposed generally adjacent the threaded protrusion 260 and extends generally radially inwardly from circumferential surface 262 and defines a flat wall 272, which is disposed radially inwardly of the circumferential surface 262 and two mutually opposed shoulders generally bounding the flat wall 272, a rearwardly facing shoulder 274 disposed adjacent the threaded protrusion 260 and a forwardly facing surface 276. A second cut-out 280 is formed along a portion of the length of the longitudinal shaft 250. The second cut-out 280 is disposed generally adjacent the flange 252 and extends generally radially inwardly from circumferential surface 262 and defines a flat wall 282, which is disposed radially inwardly of the circumferential surface 262 and two mutually opposed shoulders generally bounding the flat wall 282, a rearwardly facing shoulder 284 and a forwardly facing surface 286 disposed adjacent the flange 252.

It is a further particular feature of an embodiment of the present invention that the flat wall 272 of the first cut-out 270 and the flat wall 282 of the second cut-out 280 are preferably facing in two different angular directions and are preferably disposed at an angle of approximately 90 degrees with respect to each other. Alternatively, any other angular direction of the flat walls 272 and 282 are within the scope of the embodiments of the present invention. The two flat walls 272 and 282 are disposed generally in a different location along the longitudinal axis 103, and preferably partially overlap longitudinally, such that the rearwardly facing shoulder 284 is forwardly spaced from the forwardly facing shoulder 276.

It is specifically seen in FIG. 16D that a longitudinal groove 288 is formed on the longitudinal shaft 250.

It is noted that an indication for the medicament mixing operative orientation and for the injection operative orientation is provided on the respective flat walls 272 and 282 of the plunger rod 230. The indication may be provided in form of text, symbol, illustration or any other form of visual indication.

It is a particular feature of an embodiment of the present invention that the length of the flat wall 272 defines the length of the travel path of the plunger rod 230 relative to the syringe barrel 104 during the medicament mixing operative orientation. It is a further particular feature of an embodiment of the present invention that the length of the flat wall 282 defines the length of the travel path of the plunger rod 230 relative to the syringe barrel 104 during the pre-injection and injection operative orientations.

Figure 17A:
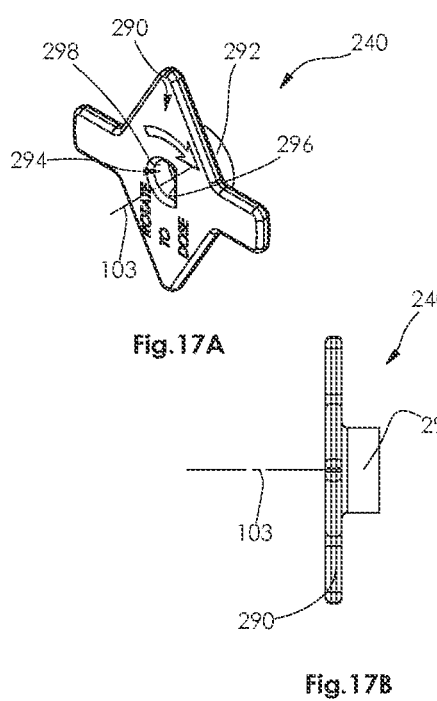
FIGS. 17A, 17B, 17C and 17D are respectively a simplified perspective view, two simplified plan side views and a simplified sectional view taken along lines D-D in FIG. 17B of a restricting element forming part of the dual chamber syringe of FIGS. 14 & 15.
Figure 17B:
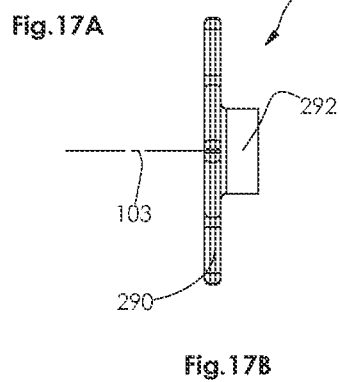
Figure 17C:
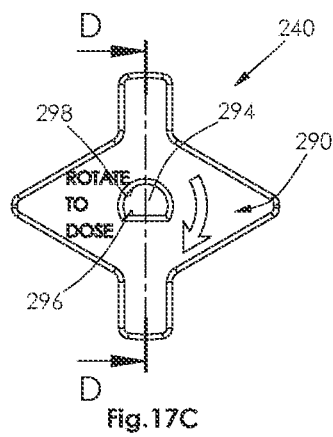
Figure 17D:
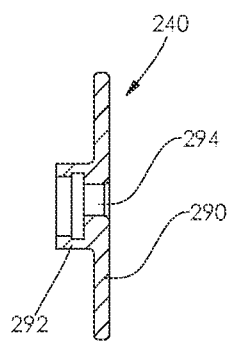

Reference is now made to FIGS. 17A, 17B, 17C and 17D, which are respectively a simplified perspective view, two simplified plan side views and a simplified sectional view taken along lines D-D in FIG. 17B of the restricting element 240 forming part of the dual chamber syringe 200 of FIGS. 14 & 15.

The restricting element 240 preferably is an integrally formed flange-like preferably flat portion 290, having a generally hollow cylindrical fixating portion 292 protruding transversely therefrom along longitudinal axis 103 and adapted for attaching the restricting element 240 to the finger grip 120.

A D-shaped slot 294 is formed in the flat portion 290 of the restricting element 240. The D-shaped slot 294 preferably defines a flat wall portion 296 and a circumferential wall portion 298. The D-shaped slot 294 communicates with the hollow fixating portion 292 and extends along longitudinal axis 103.

It is noted that an indication for enabling medicament injection is preferably provided on the flat portion 290 of the restricting element 240. The indication may be provided in form of text, symbol, illustration or any other form of visual indication.

Reference is now made to FIGS. 18A, 18B, 18C and 18D, which are simplified drawings of the dual chamber syringe 200 of FIGS. 14-17D in a storage operative orientation, including respectively a simplified pictorial view, a simplified plan side view and two simplified sectional views taken along lines C-C in FIG. 18B and lines D-D in FIG. 18C.

It is seen in FIGS. 18A-18D that the dual chamber syringe 200 is arranged along the longitudinal axis 103.

The protection cover 210 is preferably fixedly attached to the forward end 106 of the syringe barrel 104 and seals a luer of the syringe barrel 104. The plunger rod 230 is partially slidably inserted into the syringe barrel 104 through a bore formed in the finger grip 120 and engages the rearward piston 126.

It is a particular feature of an embodiment of the present invention that the restricting element 240 is operatively engaged with the plunger rod 230. The restricting element 240 is rotatable about longitudinal axis 103 relative to both the finger grip 120 and the plunger rod 230 in some operative orientations, as described in detail hereinbelow, while the finger grip 120 and the plunger rod 230 are restrained from rotation. Specifically, the finger grip 120 is fixedly attached to the rearward end of the syringe barrel 104 and a protrusion 298 is made on the inner surface of the finger grip 120, which is inserted into groove 288 of the plunger rod 230, shown particularly in FIG. 18C, thus preventing rotation of the plunger rod 230 relative to the syringe barrel 104.

It is particularly seen in FIGS. 18A-18D that in this storage operative orientation the plunger rod 230 is inserted through the D-shaped slot 294 of the restricting element 240, such that the flat wall 272 of the plunger element 230 engages flat wall 296 of the restricting element 240. In this storage operative orientation, before medicament mixing is initiated, the forwardly facing shoulder 276 of the first cut-out 270 of the plunger rod 230 is rearwardly spaced from the restricting element 240.

It is additionally seen in FIG. 18C that the intermediate piston 124 is sealingly slidably disposed with respect to the inner surface of the syringe barrel 104 and is located generally between the rearward end 108 of the syringe barrel 104 and between the bypass protrusion 128.

It is noted that a first substance is confined between the forward piston 122 and the intermediate piston 124 and the second substance is confined between the intermediate piston 124 and the rearward piston 126.

Reference is now made to FIGS. 19A, 19B, 19C and 19D, which are simplified drawings of the dual chamber syringe 200 of FIGS. 14-17D in an end of medicament mixing operative orientation, including respectively a simplified pictorial view, a simplified plan side view and two simplified sectional views taken along lines C-C in FIG. 19B and lines D-D in FIG. 19C.

It is noted that all spatial relationships between the various components of the dual chamber syringe 200 remain essentially the same as described hereinabove with respect to the storage operative orientation, besides that the plunger rod 230 is further axially forwardly longitudinally displaced relative to the syringe barrel 104 to provide for passage of solvent into medicament chamber.

It is seen in FIGS. 19A-19D that the plunger rod 230 is further axially forwardly advanced relative to the syringe barrel 104 whereas the flat wall portion 296 of the restricting element 240 is guided along the flat wall 272 of the plunger rod 230 up to engagement of the forwardly facing shoulder 276 of the plunger rod 230 with the restricting element 240 in this operative orientation.

It is a particular feature of an embodiment of the present invention that the plunger rod 230 is operatively coupled with the restricting element 240, whereas the plunger rod 230 has a restricting feature, such as cut-out 270, which is adapted to cooperate with the restricting element 240, such that upon positioning of the restricting element 240 in the injection disabling position, the plunger rod 230 is permitted to be displaced axially longitudinally forwardly only up to a certain longitudinal extent and prevented from being displaced further axially. Upon positioning of the restricting element 240 in the injection enabling position, the plunger rod 230 is permitted to be further displaced axially forwardly along longitudinal axis 103.

Specifically, the forwardly facing shoulder 276 of the plunger rod 230 now engages the restricting element 240, thus preventing further forward displacement of the plunger rod 230. It is thus appreciated that once medicament mixing is completed, the plunger rod 230 is prevented from initiating injection of the diluted medicament by means of operative engagement of the plunger rod 230 and the restricting element 240, namely by engagement between the flat wall portion 296 of the restricting element 240 with the first cut-out 270 of the plunger rod 230.

It is a particular feature of an embodiment of the present invention that, as seen in FIGS. 19A-19D, the dual-chamber syringe 200 is disposed in end of medicament mixing operative orientation and the restrictor element 240 is disposed in an injection disabling position, thus preventing further forward displacement of the plunger rod 230 relative to the syringe barrel 104.

During the medicament mixing, one of the substances contained in a first chamber passes into another chamber containing another substance through at least one of the bypass protrusions 128 of the syringe barrel 104 in order to mix the substances resulting in a liquid medicament solution now contained between the forward piston 122 and the intermediate piston 124.

It is seen that in the end of medicament mixing, as shown in FIGS. 19A-19D, the entire amount of the first substance passed into the chamber containing the second substance and created liquid medicament solution.

It is noted that alternatively more than two chambers can be provided within the syringe barrel 104, divided by more than one piston, and thus more than two substances can be mixed using several longitudinally spaced bypass protrusions 128 during various mixing stages before the injection of medication can take place.

Reference is now made to FIGS. 20A, 20B, 20C and 20D, which are simplified drawings of the dual chamber syringe 200 of FIGS. 14-17D in an injection enablement operative orientation, including respectively a simplified pictorial view, a simplified plan side view and two simplified sectional views taken along lines C-C in FIG. 20B and lines D-D in FIG. 20C.

It is a particular feature of an embodiment of the present invention that the restricting element 240 is transitioned into an injection enabling position in order to permit further forward displacement of the plunger rod 230 relative to the syringe barrel 104 and thereby facilitate ejection of the liquid medicament solution from the syringe barrel through a needle, upon attachment of the needle thereto.

It is a further particular feature of an embodiment of the present invention that in order to transition the restricting element 240 into the injection enabling position, the restricting element 240 is rotated about longitudinal axis 103, preferably at 90 degrees, so that the flat wall portion 296 of the restricting element 240 now engages the second cut-out 280 of the plunger rod 230.

Following the transition of the restricting element 240 into the injection enabling position, the longitudinal shaft 250 of the plunger rod 230 is guided longitudinally forwardly while the flat wall portion 296 is guided along flat wall portion 282 of the second cut-out 280 of the plunger rod 230.

It is a further particular feature of an embodiment of the present invention that an additional transition point may be formed on the plunger rod 230 in case it is desired to permit injection of a certain dosage and then prevent additional injection of medicament until the restricting element 240 is again transitioned to another rotational orientation. In this case, another cut-out may be formed on the plunger rod 230 and disposed rearwardly of the second cut-out 280 and at another angular orientation. This kind of mechanism can also be useful in controlling the injection speed of the medicament through needle 198.

Reference is now made to FIGS. 21A, 21B and 21C, which are simplified drawings of the dual chamber syringe 200 of FIGS. 14-17D in a pre-injection operative orientation, including respectively a simplified pictorial view, a simplified plan side view and a simplified sectional view taken along lines C-C in FIG. 21B.

It is noted that all spatial relationships between the various components of the dual chamber syringe 200 remain essentially the same as described hereinabove with respect to the injection enablement operative orientation, besides that the plunger rod 230 is further axially forwardly displaced relative to the syringe barrel 104 to position the forward piston 122 in place for initiation of injection of liquid medicament solution through the needle 198.

Figure 22A:
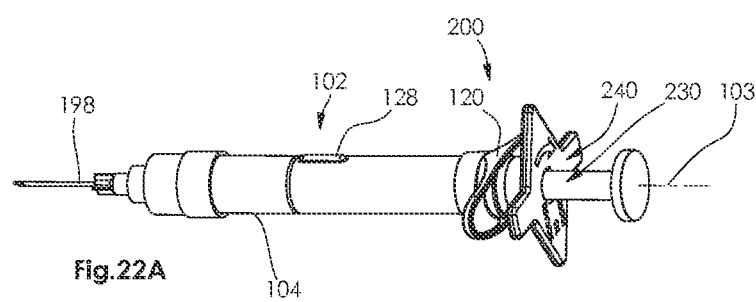
FIGS. 22A, 22B and 22C are simplified drawings of the dual chamber syringe of FIGS. 14-17D in a needle attachment operative orientation, including respectively a simplified pictorial view, a simplified plan side view and a simplified sectional view taken along lines C-C in FIG. 22B.
Figure 22B:
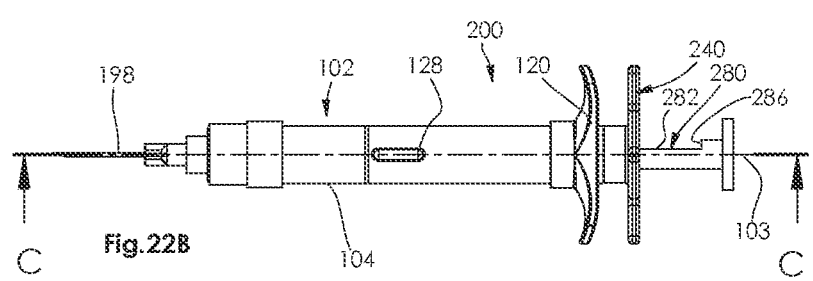
Figure 22C:
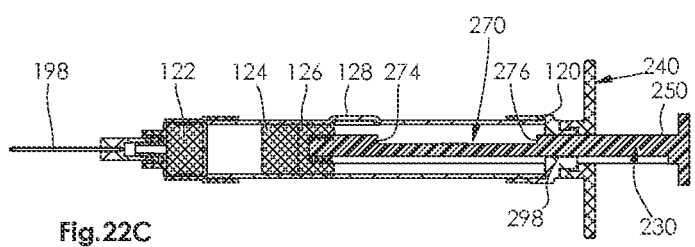

Reference is now made to FIGS. 22A, 22B and 22C, which are simplified drawings of the dual chamber syringe 200 of FIGS. 14-17D in a needle attachment operative orientation, including respectively a simplified pictorial view, a simplified plan side view and a simplified sectional view taken along lines C-C in FIG. 22B.

It is noted that all spatial relationships between the various components of the dual chamber syringe 200 remain essentially the same as described hereinabove with respect to pre-injection enablement operative orientation, besides that the needle 198 is attached to the syringe assembly 102.

Reference is now made to FIGS. 23A, 23B and 23C, which are simplified drawings of the dual chamber syringe 200 of FIGS. 14-17D in an end of injection operative orientation, including respectively a simplified pictorial view, a simplified plan side view and a simplified sectional view taken along lines C-C in FIG. 23B.

It is noted that all spatial relationships between the various components of the dual chamber syringe 200 remain essentially the same as described hereinabove with respect to needle attachment operative orientation, besides that the plunger rod 230 is further axially displaced relative to syringe barrel 104 to provide ejection of the entire medicament solution through the needle 198. In this operative orientation, all three pistons 122, 124 and 126 are in their forwardmost position.

Reference is now made to FIG. 24, which is a simplified pictorial view of an assembled dual chamber syringe 300 constructed and operative in accordance with still another embodiment of the present invention and to FIG. 25, which is a simplified pictorial exploded view of the dual chamber syringe 300 of FIG. 24.

A dual chamber syringe 300 constructed and operative in accordance with another embodiment of the present invention is described and illustrated in FIGS. 24 & 25. Some of the elements of the dual chamber syringe 300 are similar or identical to the elements of dual chamber syringe 200, which is described with reference to FIGS. 14-23C. Same elements are designated with same reference numerals.

As seen in FIGS. 24 and 25, the dual chamber syringe 300 preferably includes a syringe assembly 102 arranged along a longitudinal axis 103. The syringe assembly 102 has a syringe barrel 104 having a forward end 106 and a rearward end 108, a luer lock hub 109 fixedly attached to the forward end 106 of the syringe barrel and a cover 310. It is appreciated that the syringe assembly 102 is substantially similar to that described in U.S. patent application Ser. No. 16/994, 596, the disclosure of which is hereby incorporated by reference in its entirety.

It is also seen in FIGS. 24 & 25 that a finger grip 320 is fixedly connected or integrally made with the rearward end 108 of the syringe barrel 104. The syringe assembly 102 also preferably includes three pistons, namely a forward piston 122, an intermediate piston 124 and a rearward piston 126, which are contained within the syringe barrel 104 and are adapted for slidable axial displacement relative to the syringe barrel 104. It is appreciated that a first substance is preferably confined between one pair of the pistons and a second substance is preferably confined between another pair of the pistons and upon appropriate longitudinal displacement of the pistons, the two substances are configured for mixing and subsequent ejection, as described in detail hereinbelow.

The syringe barrel 104 is preferably made of glass and may alternatively be made of plastic. The syringe barrel 104 has a generally cylindrical shape and extends along the longitudinal axis 103. A bypass protrusion 128 is disposed generally at an intermediate location of the syringe barrel 104 along axis 103. The bypass protrusion 128 generally extends radially outwardly from an outer surface of the syringe barrel 104 to facilitate fluid passage between the two chambers formed within the syringe barrel 104 between each pair of pistons.

It is appreciated that syringe assembly 102 can be any type of conventional container, such as a cartridge commercially available from Schott Pharmaceutical Systems, Mainz, Germany or Vetter Pharma International USA Inc., IL, USA or Nuova Ompi S.r.l., Padua, Italy or may be any other suitable syringe or cartridge.

A plunger rod, which is identical to plunger rod 130, described in detail hereinabove, is arranged along the longitudinal axis 103 and is adapted to be slidably received within the syringe barrel 104. A restricting element 340 is configured to be moveably coupled to the finger grip 320 and to be operatively associated with the plunger rod 130.

It is a particular feature of an embodiment of the present invention that the restricting element 340 restricts displacement of the plunger rod 130 relative to the syringe barrel 104 in certain operative orientations and enables displacement of the plunger rod 130 relative to the syringe barrel 104 in other operative orientations.

Figure 26A:
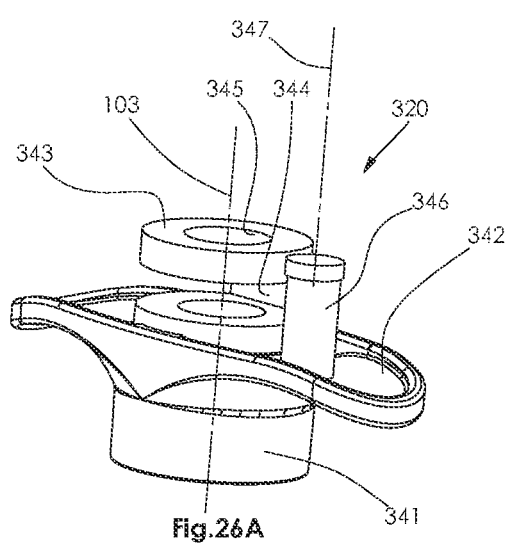
FIGS. 26A, 26B and 26C are respectively a simplified perspective view, a simplified plan side view and a simplified sectional view taken along lines C-C in FIG. 26B of a finger grip forming part of the dual chamber syringe of FIGS. 24 & 25.
Figure 26B:
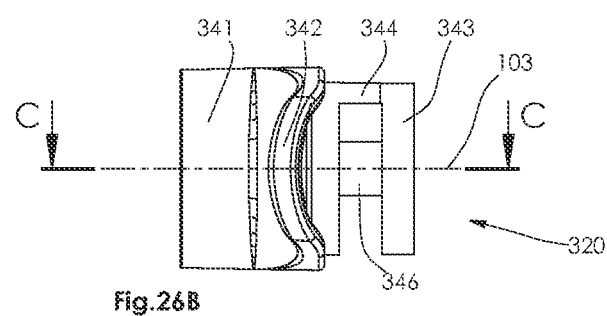
Figure 26C:
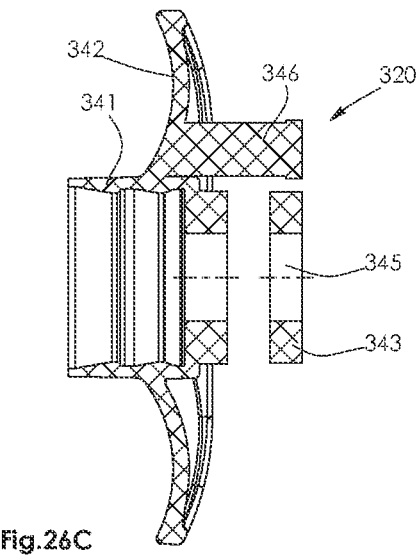

Reference is now made to FIGS. 26A, 26B and 26C, which are respectively a simplified perspective view, a simplified plan side view and a simplified sectional view taken along lines C-C in FIG. 26B of the finger grip 320 forming part of the dual chamber syringe 300 of FIGS. 24 & 25.

The finger grip 320 preferably includes a generally cylindrical hub 341, having typically two laterally extending finger grip protrusions 342 and a flange-like rearward portion 343, which is rearwardly spaced from the hub 341 and connected thereto by connecting wall 344. A through bore 345 is preferably formed within the rearward portion 343. A hinge 346 is formed on one of the finger grip protrusions 342 and extends along axis 347, generally in parallel with the cylindrical hub 341 and adjacent thereto.

Reference is now made to FIGS. 27A and 27B, which are respectively a simplified perspective view and a simplified plan side view of the restricting element 340 forming part of the dual chamber syringe 300 of FIGS. 24 & 25.

The restricting element 340 preferably is an integrally formed flange-like preferably flat longitudinal element arranged along longitudinal axis 389.

A bore 390 is formed through the restricting element 340. A fixating cut-out 392 is formed adjacent the bore 390.

Reference now made to FIGS. 28A, 28B, 28C and 28D, which are simplified drawings of the dual chamber syringe 300 of FIGS. 24-27B in a storage operative orientation, including respectively a simplified pictorial view, a simplified plan side view and two simplified sectional views taken along lines C-C in FIG. 28B and lines D-D in FIG. 28C.

It is seen in FIGS. 28A-28D that the dual chamber syringe 300 is arranged along the longitudinal axis 103.

The cover 310 is preferably coupled to the forward end 106 of the syringe barrel 104 and seals a needle 198. The plunger rod 130 is partially slidably inserted into the syringe barrel 104 through bore 345 formed in the finger grip 320 and engages the rearward piston 126.

It is a particular feature of an embodiment of the present invention that the restricting element 340 is operatively engaged with the plunger rod 130 and is hingedly supported between the finger grip protrusions 342 and between the rearward portion 343 of the finger grip 320. The restricting element 340 is hingedly supported by the finger grip 320 by means of insertion of the hinge 346 of the finger grip 320 within bore 390 of the restricting element 340.

It is noted that the restricting element 340 is arranged along axis 389, which extends generally transversely to longitudinal axis 103.

It is particularly seen in FIGS. 28A-28D that in this storage operative orientation the cut-out 170 of the plunger rod 130 is engaged within the cut-out 392 of the restricting element 340, thus flat wall 172 of the plunger rod 130 is guided within cut-out 392 of the restricting element 340. In this storage operative orientation, before medicament mixing is initiated, the restricting element 340 is supported against rearwardly facing shoulder 174 of the plunger rod 130, as specifically seen in FIG. 28C.

It is additionally seen in FIG. 28C that the intermediate piston 124 is sealingly slidably disposed with respect to the inner surface of the syringe barrel 104 and is located generally between the rearward end 108 of the syringe barrel 104 and between the bypass protrusion 128.

It is noted that a first substance is confined between the forward piston 122 and the intermediate piston 124 and a second substance is confined between the intermediate piston 124 and the rearward piston 126.

It is noted that an indication for enabling medicament injection is preferably provided on the restricting element 340. The indication may be provided in form of text, symbol, illustration or any other form of visual indication.

Figure 29A:
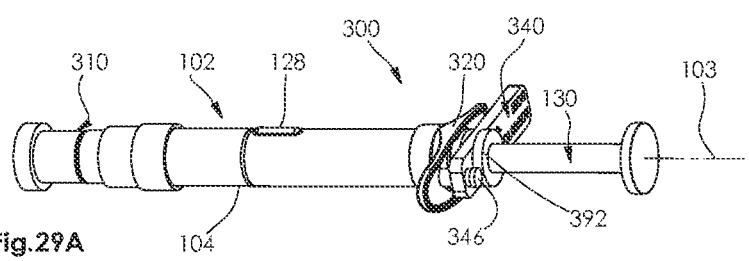
FIGS. 29A, 29B, 29C and 29D are simplified drawings of the dual chamber syringe of FIGS. 24-27B in an end of medicament mixing operative orientation, including respectively a simplified pictorial view, a simplified plan side view and two simplified sectional views taken along lines C-C in FIG. 29B and lines D-D in FIG. 29C.
Figure 29B:
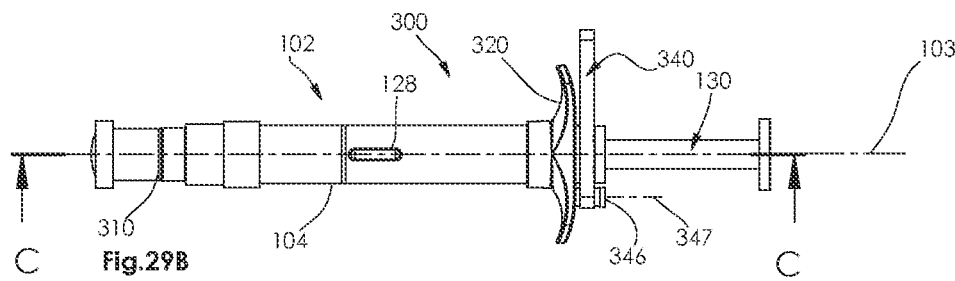
Figure 29C:
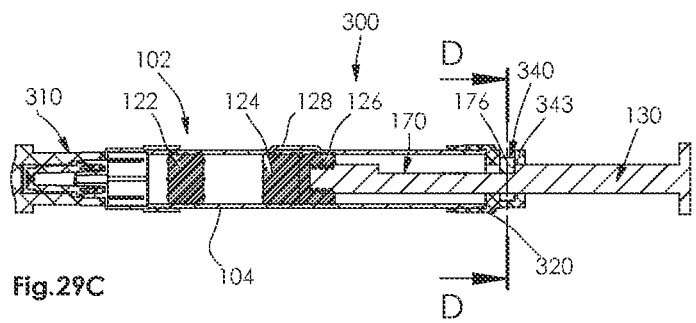
Figure 29D:
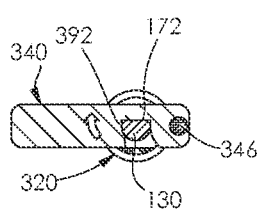

Reference is now made to FIGS. 29A, 29B, 29C and 29D, which are simplified drawings of the dual chamber syringe 300 of FIGS. 24-27B in an end of medicament mixing operative orientation, including respectively a simplified pictorial view, a simplified plan side view and two simplified sectional views taken along lines C-C in FIG. 29B and lines D-D in FIG. 29C.

It is noted that all spatial relationships between the various components of the dual chamber syringe 300 remain essentially the same as described hereinabove with respect to the storage operative orientation, besides that the plunger rod 130 is further axially forwardly longitudinally displaced relative to the syringe barrel 104 to provide for passage of solvent into medicament chamber.

It is seen in FIGS. 29A-29D that the plunger rod 130 is axially forwardly advanced relative to the syringe barrel 104 whereas the cut-out 392 of the restricting element 340 is guided along the flat wall 172 of the plunger rod 130 up to engagement of the forwardly facing shoulder 176 of the plunger rod 130 with the restricting element 340 in this operative orientation.

It is a particular feature of an embodiment of the present invention that the plunger rod 130 is operatively coupled with the restricting element 340, whereas the plunger rod 130 has a restricting feature, such as cut-out 170, which is adapted to cooperate with the restricting element 340, such that upon positioning of the restricting element 340 in the injection disabling position, the plunger rod 130 is permitted to be displaced axially longitudinally forwardly only up to a certain longitudinal extent and prevented from being displaced further axially. Upon positioning of the restricting element 340 in the injection enabling position, the plunger rod 130 is permitted to be further displaced axially forwardly along longitudinal axis 103.

Specifically, the forwardly facing shoulder 176 of the plunger rod 130 now engages the restricting element 340, thus preventing further forward displacement of the plunger rod 130. It is thus appreciated that once medicament mixing is completed, the plunger rod 130 is prevented from initiating injection of the diluted medicament by means of operative engagement of the plunger rod 130 and the restricting element 340, namely by engagement between the cut-out 392 of the restricting element 340 with the cut-out 170 of the plunger rod 130.

It is a particular feature of an embodiment of the present invention that, as seen in FIGS. 29A-29D, the dual-chamber syringe 300 is disposed in end of medicament mixing operative orientation and the restrictor element 340 is disposed in an injection disabling position, thus preventing further forward displacement of the plunger rod 130 relative to the syringe barrel 104.

During the medicament mixing, one of the substances contained in a first chamber passes into another chamber containing another substance through at least one of the bypass protrusions 128 of the syringe barrel 104 in order to mix the substances resulting in a liquid medicament solution now contained between the forward piston 122 and the intermediate piston 124.

It is seen that in the end of medicament mixing, as shown in FIGS. 29A-29D, the entire amount of the first substance passed into the chamber containing the second substance and created liquid medicament solution.

It is noted that alternatively more than two chambers can be provided within the syringe barrel 104, divided by more than one piston, and thus more than two substances can be mixed using several longitudinally spaced bypass protrusions 128 during various mixing stages before the injection of medication can take place.

Reference is now made to FIGS. 30A, 30B, 30C and 30D, which are simplified drawings of the dual chamber syringe of FIGS. 24-27B in an injection enablement operative orientation, including respectively a simplified pictorial view, a simplified plan side view and two simplified sectional views taken along lines C-C in FIG. 30B and lines D-D in FIG. 30C;

It is noted that all spatial relationships between the various components of the dual chamber syringe 300 remain essentially the same as described hereinabove with respect to the end of medicament mixing operative orientation, besides the following:

It is a particular feature of an embodiment of the present invention that the restricting element 340 is now transitioned to an injection enabling position in order to permit further forward displacement of the plunger rod 130 relative to the syringe barrel 104 and thereby facilitate ejection of the liquid medicament solution from the syringe barrel 104 through a needle, upon its attachment thereto.

It is a further particular feature of an embodiment of the present invention that in order to transition the restricting element 340 into the injection enabling position, the restricting element 340 is rotated about longitudinal axis 347, so that the restricting element 340 does not engage the plunger rod 130 anymore. It is noted that rotation of the restricting element 340 in accordance with an embodiment of the present invention, requires only overcoming the friction between the plunger rod 130 an the restricting element 340.

Following the transition of the restricting element 340 into the injection enabling position, the plunger rod 130 can be freely displaced longitudinally forwardly along longitudinal axis 103 and the restricting element 340 is retained on the finger grip 320 without interfering with the plunger rod 130 in this operative orientation.

Reference is now made to FIGS. 31A, 31B, 31C and 31D, which are simplified drawings of the dual chamber syringe 300 of FIGS. 24-27B in a needle attachment operative orientation, including respectively a simplified pictorial view, a simplified plan side view and two simplified sectional views taken along lines C-C in FIG. 31B and lines D-D in FIG. 31C.

It is noted that all spatial relationships between the various components of the dual chamber syringe 300 remain essentially the same as described hereinabove with respect to injection enablement operative orientation, besides that the needle 198 is attached to the syringe assembly 102 and that the plunger rod 130 is further axially forwardly displaced relative to the syringe barrel 104 to position the forward piston 122 in place for initiation of injection of liquid medicament solution through the needle 198.

Reference is now made to FIGS. 32A, 32B, 32C and 32D, which are simplified drawings of the dual chamber syringe 300 of FIGS. 24-27B in an end of injection operative orientation, including respectively a simplified pictorial view, a simplified plan side view and two simplified sectional views taken along lines C-C in FIG. 32B and lines D-D in FIG. 32C.

It is noted that all spatial relationships between the various components of the dual chamber syringe 300 remain essentially the same as described hereinabove with respect to needle attachment operative orientation, besides that the plunger rod 130 is further axially displaced relative to syringe barrel 104 to provide ejection of the entire medicament solution through the needle 198. In this operative orientation, all three pistons 122, 124 and 126 are in their forwardmost position.

Reference is now made to FIG. 33A, which is a simplified pictorial view of an assembled dual chamber syringe constructed and operative in accordance with yet another embodiment of the present invention and to FIG. 33B, which is a simplified pictorial exploded view of the dual chamber syringe of FIG. 33A.

As seen in FIGS. 33A and 33B, a dual chamber syringe 400 preferably includes a syringe assembly 102 arranged along a longitudinal axis 103. The syringe assembly 102 has a syringe barrel 104 having a forward end 106 and a rearward end 108 and a cover 410, which is preferably removably connected to the proximal end 106 of the syringe barrel 104. It is appreciated that the syringe assembly 102 is substantially similar to that described in U.S. patent application Ser. No. 16/994,596, the disclosure of which is hereby incorporated by reference in its entirety.

It is also seen in FIGS. 33A & 33B that a finger grip 120 is fixedly connected or integrally made with the rearward end 108 of the syringe barrel 104. The syringe assembly 102 also preferably includes three pistons, namely a forward piston 122, an intermediate piston 124 and a rearward piston 126, which are contained within the syringe barrel 104 and are adapted for slidable axial displacement relative to the syringe barrel 104. It is appreciated that a first substance is preferably confined between one pair of the pistons and a second substance is preferably confined between another pair of the pistons and upon appropriate longitudinal displacement of the pistons, the two substances are configured for mixing and subsequent ejection, as described in detail hereinbelow.

The syringe barrel 104 is preferably made of glass and may be alternatively made of plastic. The syringe barrel 104 has a generally cylindrical shape and extends along the longitudinal axis 103. A bypass protrusion 128 is disposed generally at an intermediate location of the syringe barrel 104 along axis 103. The bypass protrusion 128 generally extends radially outwardly from an outer surface of the syringe barrel 104 to facilitate fluid passage between the two chambers formed within the syringe barrel 104 between each pair of pistons.

It is appreciated that syringe assembly 102 can be any type of conventional container, such as a cartridge commercially available from Schott Pharmaceutical Systems, Mainz, Germany or Vetter Pharma International USA Inc., IL, USA or Nuova Ompi S.r.l., Padua, Italy or may be any other suitable syringe or cartridge.

A plunger rod assembly 430 is arranged along the longitudinal axis 103 and preferably includes a plunger rod outer portion 432 and a plunger rod inner portion 434, which is insertable into the plunger rod outer portion 432. The plunger rod assembly 430 is adapted to be slidably received within the syringe barrel 104 and to be operatively associated with the finger grip 120. A restricting element 140, which is described in detail hereinabove, is configured to be operatively coupled with the plunger rod assembly 430.

It is a particular feature of an embodiment of the present invention that the restricting element 140 restricts displacement of the plunger rod assembly 430 relative to the syringe barrel 104 in certain operative orientations and enables displacement of the plunger rod assembly 430 relative to the syringe barrel 104 in other operative orientations.

Reference is now made to FIGS. 34A, 34B and 34C, which are respectively a simplified perspective view, a simplified plan side view and a simplified sectional view taken along lines C-C in FIG. 34B of the outer portion 432 of the plunger rod 430 forming part of the dual chamber syringe 400 of FIGS. 33A & 33B.

The plunger rod outer portion 432 preferably is an integrally formed element, preferably injection molded of plastic and is arranged along longitudinal axis of symmetry 103.

The plunger rod outer portion 432 preferably includes a longitudinal shaft 450 terminating at a generally circular flange 452 at a rearward end thereof. The circular flange 452 extends generally radially outwardly from the outer surface of the longitudinal shaft 450 and is disposed generally transversely with respect thereto. An externally threaded protrusion 460 extends forwardly from a forward end of the longitudinal shaft 450. The longitudinal shaft 450 is preferably generally cylindrical, defining an outer circumferential surface 462.

It is a particular feature of an embodiment of the present invention that a window 470 is formed along a portion of the length of the longitudinal shaft 450. The window 470 defines two mutually opposed shoulders generally bounding the window 470, a rearwardly facing shoulder 474 and a forwardly facing shoulder 476.

It is a particular feature of an embodiment of the present invention that the length of the window 470 defines the length of the travel path of the plunger rod assembly 430 relative to the syringe barrel 104 during the medicament mixing operative orientation.

The plunger rod outer portion 432 includes a through bore 480 terminating adjacent the externally threaded portion 460. The through bore 480 communicates with the window 470.

Reference is now made to FIGS. 35A, 35B and 35C, which are respectively a simplified perspective view and two simplified plan side views of the inner portion 434 of the plunger rod 430 forming part of the dual chamber syringe 400 of FIGS. 33A & 33B.

The plunger rod inner portion 434 preferably is an integrally formed element, preferably injection molded of plastic and is arranged along longitudinal axis of symmetry 103.

The plunger rod inner portion 434 preferably includes a longitudinal shaft 490 terminating at a generally circular flange 492 at a rearward end thereof and at a forwardly facing edge 494 at a forward end thereof. The circular flange 492 extends generally radially outwardly from the outer surface of the longitudinal shaft 490 and is disposed generally transversely with respect thereto. The longitudinal shaft 490 is preferably generally cylindrical, defining an outer circumferential surface 496.

It is a particular feature of an embodiment of the present invention that a spiral surface 500 is formed along a portion of the length of the longitudinal shaft 490. The spiral surface 500 preferably extends rearwardly from the forwardly facing edge 494 and terminates at a forwardly facing shoulder 502 at an intermediate location along the length of the longitudinal shaft 490.

Figure 36A:
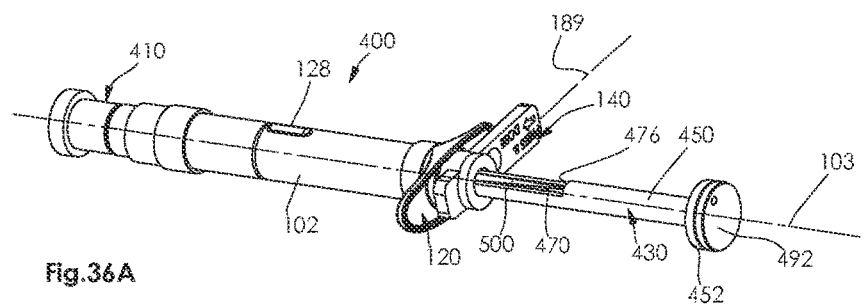
FIGS. 36A, 36B, 36C and 36D are simplified drawings of the dual chamber syringe of FIGS. 33A-35C in a storage operative orientation, including respectively a simplified pictorial view, a simplified plan side view and two simplified sectional views taken along lines C-C in FIG. 36B and lines D-D in FIG. 36C.
Figure 36B:
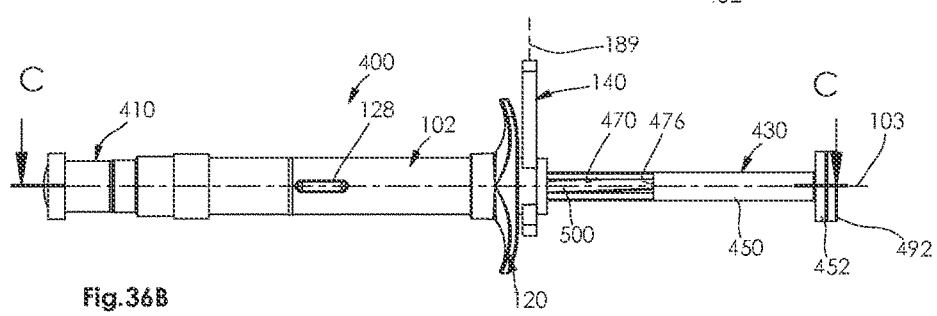
Figure 36C:
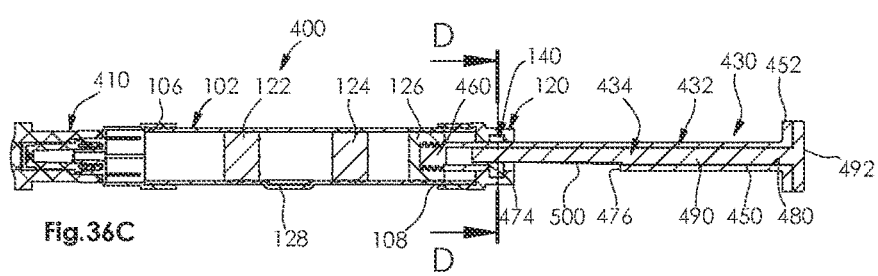

Reference is now made to FIGS. 36A, 36B, 36C and 36D, which are simplified drawings of the dual chamber syringe of FIGS. 33A-35C in a storage operative orientation, including respectively a simplified pictorial view, a simplified plan side view and two simplified sectional views taken along lines C-C in FIG. 36B and lines D-D in FIG. 36C.

It is seen in FIGS. 36A-36D that the dual chamber syringe 400 is arranged along the longitudinal axis 103.

The cover 410 is preferably removably attached to the forward end 106 of the syringe barrel 104. The plunger rod inner portion 434 is inserted into bore 480 of the plunger rod outer portion 432 to form a plunger rod assembly 430, such that the spiral surface 500 of the plunger rod inner portion 424 is disposed in front of window 470 of the plunger rod outer portion 432. The plunger rod assembly 430 is partially slidably inserted into the syringe barrel 104 through bore 146 formed in the finger grip 120 and engages the rearward piston 126.

It is a particular feature of an embodiment of the present invention that the plunger rod inner portion 434 is rotatable relative to the plunger rod outer portion 432 about longitudinal axis 103.

It is a particular feature of an embodiment of the present invention that the restricting element 140 is operatively engaged with the plunger rod assembly 430 and is supported between the rearward end 108 of the syringe barrel 104 and between the rearward portion 142 of the finger grip 120.

It is noted that the restricting element 140 is arranged along axis 189, which is extends generally transversely to longitudinal axis 103.

Figure 36D:
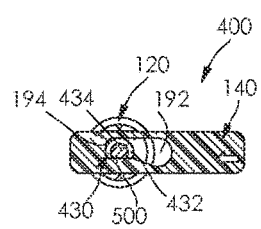

It is particularly seen in FIG. 36D that in this storage operative orientation the plunger rod assembly 430 is disposed in the narrow portion 194 of the restricting element 140, thus the narrow portion 194 engages the spiral surface 500 of the plunger rod inner portion 434. In this storage operative orientation, before medicament mixing is initiated, the restricting element 140 is supported against rearwardly facing shoulder 474 of the plunger rod outer portion 432, as specifically seen in FIG. 35C.

It is additionally seen in FIG. 36C that the intermediate piston 124 is sealingly slidably disposed with respect to the inner surface of the syringe barrel 104 and is located generally between the rearward end 108 of the syringe barrel 104 and between the bypass protrusion 128.

It is noted that a first substance is confined between the forward piston 122 and the intermediate piston 124 and a second substance is confined between the intermediate piston 124 and the rearward piston 126.

Figure 37A:
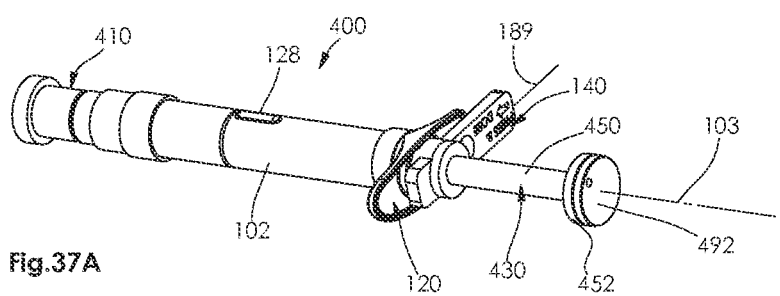
FIGS. 37A, 37B, 37C and 37D are simplified drawings of the dual chamber syringe of FIGS. 33A-35C in an end of medicament mixing operative orientation, including respectively a simplified pictorial view, a simplified plan side view and two simplified sectional views taken along lines C-C in FIG. 37B and lines D-D in FIG. 37C.
Figure 37B:
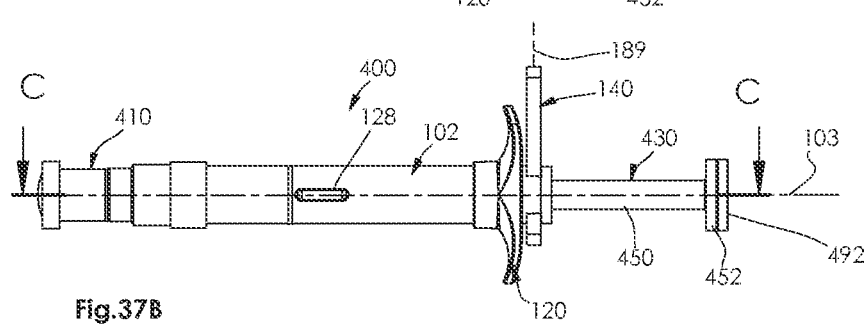
Figure 37C:
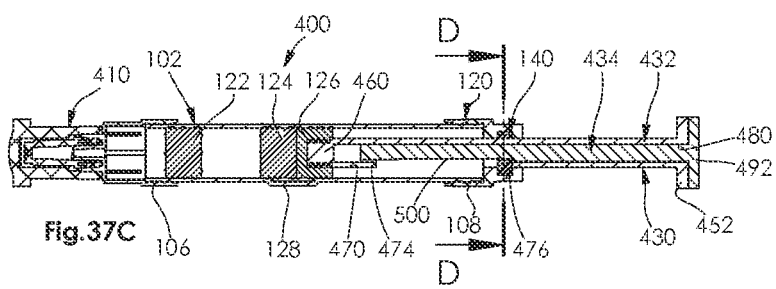
Figure 37D:
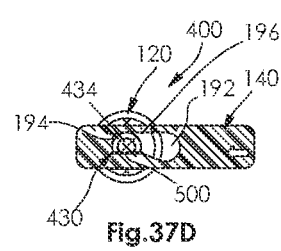

Reference is now made to FIGS. 37A, 37B, 37C and 37D, which are simplified drawings of the dual chamber syringe 400 of FIGS. 33A-35C in an end of medicament mixing operative orientation, including respectively a simplified pictorial view, a simplified plan side view and two simplified sectional views taken along lines C-C in FIG. 37B and lines D-D in FIG. 37C.

It is seen in FIGS. 37A-37C that the plunger rod assembly 430 is axially forwardly advanced relative to the syringe barrel 104 whereas the narrow portion 194 of the restricting element 140 is guided along the spiral surface 500 of the plunger rod inner portion 434, in this operative orientation.

It is a particular feature of an embodiment of the present invention that the mixing speed is controlled due to operative engagement between the restricting element 140 and the plunger rod assembly 430. Specifically, while the plunger rod assembly 430 is advanced axially forwardly, the narrow portion 194 of the restricting element 140 is guided along spiral surface 500 of the plunger rod inner portion 434, thus urges rotation of the plunger rod inner portion 434 relative to the restricting element 140 and to the plunger rod outer portion 432.

It is a further particular feature of an embodiment of the present invention that the mixing speed is controlled due to operative engagement between the plunger rod outer portion 432 and plunger rod inner portion 434. The outer dimeter of the plunger rod inner portion 434 can be slightly smaller than the inner diameter of the plunger rod outer portion 432, thus friction between the plunger rod outer portion 432 and the plunger rod inner portion 434 upon relative rotation therebetween is created only by engagement of their respective flanges 452 and 492. Alternatively, the plunger rod inner portion 434 can be inserted in a friction-fit manner into the plunger rod outer portion 432, thus increasing the friction between the two portions of the plunger rod assembly 430.

Friction between the two portions of the plunger rod assembly 430 facilitates controlling the rotation speed of the two plunger rod portions 432 and 434 and thereby controlling the mixing speed. Additionally, the pitch of the spiral surface 500 defines the mixing speed as well due to the engagement between the narrow portion 194 of the restricting element 140 and the spiral surface 500 of the plunger rod inner portion 434, such that as the pitch of the spiral surface 500 is larger, the mixing speed is slower.

It is a further particular feature of an embodiment of the present invention that the plunger rod assembly 430 is operatively coupled with the restricting element 140, whereas the plunger rod assembly 430 has a feature, such as a window 470 and a spiral surface 500 of the plunger assembly 430, which are adapted to cooperate with the restricting element 140, such that upon positioning of the restricting element 140 in the injection disabling position, the plunger rod assembly 430 is permitted to be displaced axially forwardly only up to a certain longitudinal extent and upon positioning of the restricting element 140 in the injection enabling position, the plunger rod assembly 430 is permitted to be further displaced axially forwardly along longitudinal axis 103.

Specifically, the forwardly facing shoulder 476 of the plunger rod outer portion 432 engages the restricting element 140 at the end of medicament mixing operative orientation, thus prevents further forward displacement of the plunger rod assembly 430. It is thus appreciated that once medicament mixing is completed, the plunger rod assembly 430 is prevented from initiating injection of the diluted medicament by means of operative engagement of the plunger rod assembly 430 and the restricting element 140, namely by engagement between the narrow portion 194 of the restricting element 140 and the window 470 of the plunger rod assembly 430.

It is a particular feature of an embodiment of the present invention that, as seen in FIGS. 37A-37D, the dual-chamber syringe 400 is disposed in end of medicament mixing operative orientation and the restrictor element 140 is disposed in an injection disabling position, thus preventing further forward displacement of the plunger rod assembly 430 relative to the syringe barrel 104.

During the medicament mixing, one of the substances contained in a first chamber passes into another chamber containing another substance through at least one of the bypass protrusions 128 of the syringe barrel 104 in order to mix the substances resulting in a liquid medicament solution now contained between the forward piston 122 and the intermediate piston 124.

It is seen that in the end of medicament mixing, as shown in FIGS. 37A-37D, the entire amount of the first substance passed into the chamber containing the second substance and created liquid medicament solution.

It is noted that alternatively more than two chambers can be provided within the syringe barrel 104, divided by more than one piston, and thus more than two substances can be mixed using several longitudinally spaced bypass protrusions 128 during various mixing stages before the injection of medication can take place.

Figure 38A:
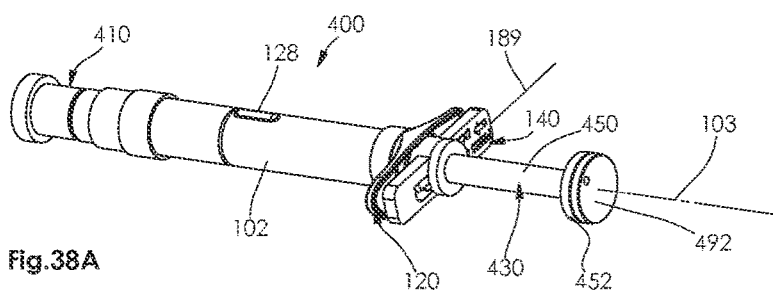
FIGS. 38A, 38B, 38C and 38D are simplified drawings of the dual chamber syringe of FIGS. 24-27B in an injection enablement operative orientation, including respectively a simplified pictorial view, a simplified plan side view and two simplified sectional views taken along lines C-C in FIG. 38B and lines D-D in FIG. 38C.
Figure 38B:
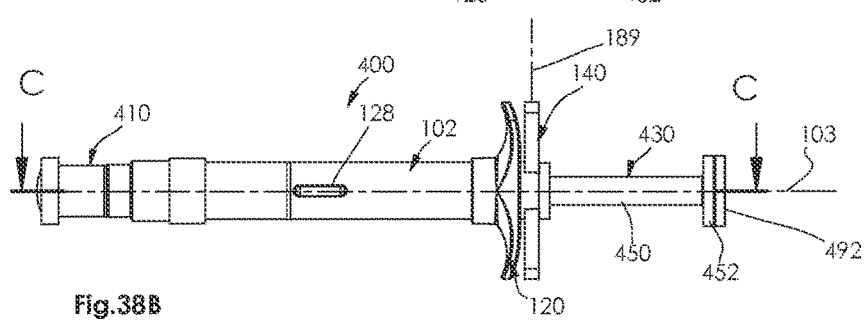
Figure 38C:
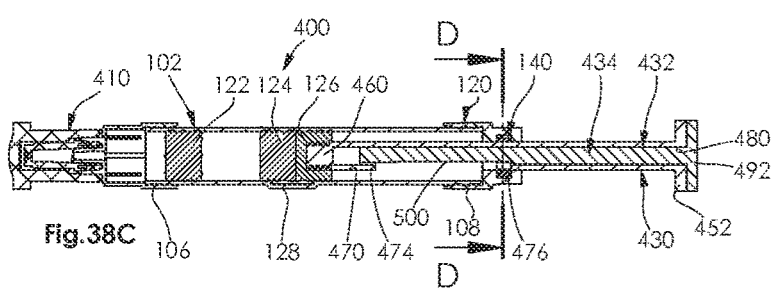
Figure 38D:
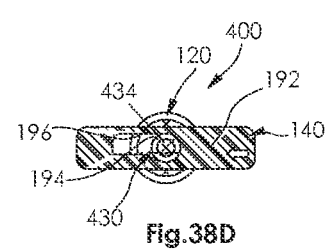

Reference is now made to FIGS. 38A, 38B, 38C and 38D, which are simplified drawings of the dual chamber syringe 400 of FIGS. 24-27B in an injection enablement operative orientation, including respectively a simplified pictorial view, a simplified plan side view and two simplified sectional views taken along lines C-C in FIG. 38B and lines D-D in FIG. 38C.

It is a particular feature of an embodiment of the present invention that the restricting element 140 is transitioned into the injection enabling position in order to permit further forward displacement of the plunger rod assembly 430 relative to the syringe barrel 104 and thereby facilitate ejection of the liquid medicament solution from the syringe barrel through the needle 198.

It is a further particular feature of an embodiment of the present invention that in order to transition the restricting element 140 into the injection enabling position, the restricting element 140 is displaced axially along axis 189. It is appreciated that the restricting element 140 is displaced transversely relative to the syringe assembly 102 and relative to the plunger rod assembly 430.

Following the transition of the restricting element 140 into the injection enabling position, the plunger rod assembly 430 is guided longitudinally forwardly through the wider portion 192 of the restricting element 140, so that the wider portion 192 of the restricting element 140 engages the outer circumferential surface 462 of the plunger rod outer portion 432, rearwardly of the cut-out 470, between the rearward end 108 of the syringe barrel 104 and the flange 452 of the plunger rod outer portion 432.

It is a further particular feature of an embodiment of the present invention that during the transitioning of the restricting element 140 from the injection disabling position to the injection enabling position, the user has to apply a certain force that is greater than a predetermined force threshold to enable the plunger rod assembly 430 to snap over the protrusions 196 of the restricting element 140.

It is noted that following positioning of the plunger rod assembly 430 in its injection enabling operative orientation, the plunger rod assembly 430 is configured to be further axially displaced relative to syringe barrel 104 to provide ejection of the entire medicament solution through the needle 198. In this end of injection operative orientation, all three pistons 122, 124 and 126 are in their forwardmost position, as illustrated specifically in FIGS. 23A-23C, for example.

It is noted that any of the features described with reference to each one of the above-mentioned embodiments can be combined together to provide additional technical advantages.

It will be appreciated by persons skilled in the art that the present invention is not limited by what has been particularly shown and described hereinabove. Rather the scope of the present invention includes both combinations and sub-combinations of various features described hereinabove as well as variations and modifications thereof which are not in the prior art.

The invention claimed is:

1. A syringe assembly, comprising:
a syringe barrel having a forward end and a rearward end and being arranged along a longitudinal axis;
a restricting element, moveably supported on a portion of said syringe assembly, and said restricting element is positionable in different operative orientations in one of:
an injection disabling position,
and an injection enabling position,
and wherein said restricting element has a flat portion that extends transversely with respect to said longitudinal axis;
a plunger rod assembly displaceable within the syringe barrel and operatively coupled with said restricting element;
the plunger rod assembly has a forwardly facing shoulder that extends transversely with respect to said longitudinal axis;
the plunger rod assembly having at least one restricting feature adapted to cooperate with said restricting element, such that;
when said restricting element is in said injection disabling position, the plunger rod assembly is displaceable axially forwardly only up to a certain longitudinal extent relative to said syringe barrel, and is prevented by said cooperation of said restricting feature and said restricting element, from further axial displacement;
and when said restricting element is in said injection enabling position, the plunger rod assembly is permitted to be further displaced axially forwardly relative to said syringe barrel and relative to said restricting element,
and wherein in order to position said restricting element in said injection enabling position, said restricting element is displaced rotatably about said longitudinal axis,
and wherein said at least one restricting feature comprises a first restricting feature is-formed along a portion of the length of said plunger rod assembly and defining a flat wall,
and wherein said restricting element has a slot with a flat edge, whereas when said restricting element is positioned in said injection disabling position, said flat edge is guided along said flat wall of said first restricting feature of said plunger rod assembly,
and further wherein upon engagement of said forwardly facing shoulder with said flat portion, the restricting element is rotatable about said longitudinal axis, and thereby positioned in said injection enabling position.

2. The syringe assembly according to claim 1, and wherein when said restricting element is positioned in said injection enabling position, further axial displacement of said plunger rod assembly relative to said syringe barrel in is permitted to permit ejection of a medicament from said syringe barrel.

3. The syringe assembly according to claim 2, and wherein the longitudinal extent of said restricting feature defines the length of the travel path of said plunger rod assembly relative to said syringe barrel during said injection enabling position.

4. The syringe assembly according to claim 1, further comprising a finger grip associated with said syringe barrel, and wherein said restricting element is supported by said finger grip.

5. The syringe assembly according to claim 1, and wherein said first restricting feature is formed along a portion of the length of said plunger rod assembly and a second restricting feature is formed along another portion of the length of said plunger rod assembly and said first and second restricting features are facing different angular directions.

6. The syringe assembly according to claim 5, and wherein said flat edge is configured for engagement with said second restricting feature of said plunger rod assembly up to an end of injection operative orientation.

7. The syringe assembly according to claim 1, wherein said flat wall prevents relative rotation between said plunger rod assembly and said restricting element, along a portion of a longitudinal extent of said flat wall.

8. The syringe assembly according to claim 1, wherein said flat wall is disposed radially inwardly of a circumferential surface of said plunger rod assembly.

9. The syringe assembly according to claim 1, wherein two mutually opposed shoulders bound the flat wall, said shoulders comprising: a rearwardly facing shoulder and said forwardly facing shoulder.

10. The syringe assembly according to claim 9, wherein in a pre-mixing medicament orientation of said syringe, the forwardly facing shoulder is rearwardly spaced from the restricting element.

11. The syringe assembly according to claim 9, wherein the plunger rod assembly is axially advanced relative to the syringe barrel whereas the flat edge of the restricting element is guided along the flat wall of the plunger rod assembly up to engagement of the forwardly facing shoulder with the restricting element.

12. A method for delivering at least one medicament to a subject, the method comprising:
providing a syringe assembly, having a syringe barrel having a forward end and a rearward end and being arranged along a longitudinal axis;
movably coupling a restricting element onto a portion of said syringe assembly, wherein said restricting element has a flat portion that extends transversely with respect to said longitudinal axis;
providing a plunger rod assembly displaceable within the syringe barrel and operatively coupled with said restricting element, the plunger rod assembly has a forwardly facing shoulder that extends transversely with respect to said longitudinal axis;
the plunger rod assembly having at least one restricting feature adapted to cooperate with said restricting element,
wherein a first restricting feature is formed along a portion of the length of said plunger rod assembly and defines a flat wall,
and wherein said restricting element has a slot with a flat edge, whereas said flat edge is guided along said flat wall of said first restricting feature of said plunger rod assembly when said restricting element is positioned in said injection disabling position;
and when said restricting element is in an injection disabling position, permitting axial forward displacement of the plunger rod assembly relative to said syringe barrel only up to a certain longitudinal extent, and preventing said plunger rod assembly from further axial displacement in order to perform medicament mixing;

said restricting element is displaced rotatably about said longitudinal axis in order to position said restricting element in said injection enabling position;

thereafter, upon engagement of said forwardly facing shoulder with said flat portion, permitting rotation of said restricting element about said longitudinal axis, thereby positioning said restricting element in said injection enabling position, thus permitting further axial forward displacement of the plunger rod assembly relative to said syringe barrel and relative to said restricting element, thereby delivering said at least one medicament to the subject.

13. The syringe assembly according to claim 12, wherein said flat wall prevents relative rotation between said plunger rod assembly and said restricting element along a portion of a longitudinal extent of said flat wall.

14. The syringe assembly according to claim 12, wherein said flat wall being disposed radially inwardly of a circumferential surface said plunger rod assembly.

15. The syringe assembly according to claim 12, wherein two mutually opposed shoulders bound the flat wall, said shoulders comprising: a rearwardly facing shoulder and said forwardly facing shoulder.

16. The syringe assembly according to claim 15, wherein the plunger rod assembly is axially advanced relative to the syringe barrel whereas the flat edge of the restricting element is guided along the flat wall of the plunger rod assembly up to engagement of the forwardly facing shoulder with the restricting element.

17. The syringe assembly according to claim 12, wherein in a pre-mixing medicament orientation of said syringe, the forwardly facing shoulder is rearwardly spaced from the restricting element.

* * * * *